(12) United States Patent
Kaneda et al.

(10) Patent No.: US 7,504,098 B2
(45) Date of Patent: Mar. 17, 2009

(54) METHOD FOR INTRODUCING A BIOLOGICAL MOLECULE USING A VIRAL ENVELOPE AND HEPARIN AND SYSTEM THEREFORE

(75) Inventors: Yasufumi Kaneda, Mino (JP); Ryuichi Morishita, Osaka (JP); Munehisa Shimamura, Mino (JP)

(73) Assignee: AnGes MG, Inc., Osaka (JP)

( * ) Notice: Subject to any disclaimer, the term of this patent is extended or adjusted under 35 U.S.C. 154(b) by 15 days.

(21) Appl. No.: 11/067,109

(22) Filed: Feb. 25, 2005

(65) Prior Publication Data

US 2006/0002894 A1 Jan. 5, 2006

Related U.S. Application Data

(63) Continuation of application No. PCT/JP2003/010675, filed on Aug. 22, 2003.

(30) Foreign Application Priority Data

Aug. 27, 2002 (JP) .............................. 2002-247812

(51) Int. Cl.
- *A01K 43/04* (2006.01)
- *A61K 31/70* (2006.01)
- *A01N 63/00* (2006.01)
- *A01N 65/00* (2006.01)
- *C12N 15/00* (2006.01)

(52) U.S. Cl. .................. 424/93.1; 514/44; 435/320.1
(58) Field of Classification Search ................ None
See application file for complete search history.

(56) References Cited

U.S. PATENT DOCUMENTS

| | | | |
|---|---|---|---|
| 4,745,053 A * | 5/1988 | Mitsuhashi | 435/5 |
| 5,631,237 A | 5/1997 | Dzau et al. | |
| 7,029,838 B2 * | 4/2006 | Williams et al. | 435/1.1 |
| 7,182,944 B2 * | 2/2007 | Bankiewicz | 424/93.2 |

FOREIGN PATENT DOCUMENTS

| | | |
|---|---|---|
| JP | 2002-247812 | 8/2002 |
| WO | WO 00/76553 | 12/2000 |
| WO | WO 01/57204 | 9/2001 |
| WO | WO 01/57204 A1 | 9/2001 |
| WO | WO 2004/035779 | 4/2004 |
| WO | WO 2004/035779 A1 | 4/2004 |

OTHER PUBLICATIONS

Summerford, et al. (1998) Journal of Virology, 72(2): 1438-45.*
Dzau et al, *Proc. Natl. Acad. Sci USA*, 93, (1996) pp. 11421-11425.
Hagihara Y. et al., *Gene Ther.*, 7, (2000) pp. 759-763.
Harrigan M.R. et al., *Neurosurgery*, 50, (2002) pp. 589-598.
Kaneda et al, *Exp Cell Res.*, 173, (1987) pp. 56-69.
Kaneda et al., *Molecular Medicine Today*, 5, (1999) pp. 298-303.
Losordo D.W. et al., *Circulation*, 98, (1998) pp. 2800-2804.
Lyons, M.K et al., *Brain Res.*, 558, (2002) pp. 315-320.
Mastakov M.Y. et al., *Mol Ther.*, 5, (2002) pp. 371-380.
Nguyen J. B., *Neuroreport*, 12, (2001) pp. 1961-1964.
Shimamura, Munehisa et al., *Biochemical & Biophysical*, 300, (2003) pp. 464-471.
Yamada K. et al., *Am J Physiol.*, 271, (1996) pp. R1212-R1220.
Yoshimura, S. et al., *Hypertension*, 39, (2002) pp. 1028-1034.
Devereux et al., "Heparin binds to murine leukaemia virus and inhibits both envelope independent attachment and infection," Database accession No. PREV200200153327, vol. 98, No. 11, Part 1 (2001).
Hirsh et al., "Heparin and Low-Molecular-Weight Heparin," *CHEST* 119:64S-94S (2001).
Kaneda et al., "Hemagglutinating Virus of Japan (HVJ) Envelope Vector as a Versatile Gene Delivery System," *Molecular Therapy*, vol. 6, No. 2, pp. 219-226 (2002).
Stedman, *Stedman's Medical Dictionary*, 28th ed, Baltimore: Lippincott Williams and Wilkins. Heparin; p. 874. Heparin U.; p. 2067 (2006).

* cited by examiner

*Primary Examiner*—Robert M Kelly
(74) *Attorney, Agent, or Firm*—James F. Haley, Jr.; Ropes & Gray LLP

(57) ABSTRACT

The object of the present invention is to provide a method of efficient delivery into a brain and central nervous system, and to provide a method of efficient delivery with a viral envelope. The present invention provides a system for introducing a biomolecule into a cell comprising A) a biomolecule; B) a viral envelope; and C) glycosaminoglycan. Further, the present invention provides a method for delivering a biomolecule into a brain, comprising the steps of: A) transiently closing an artery of the head portion or cervical portion; and B) introducing a biomolecule into the brain during the closing of the artery of the head portion or the cervical portion.

2 Claims, 6 Drawing Sheets
(5 of 6 Drawing Sheet(s) Filed in Color)

US 7,504,098 B2

METHOD FOR INTRODUCING A BIOLOGICAL MOLECULE USING A VIRAL ENVELOPE AND HEPARIN AND SYSTEM THEREFORE

This application is a continuation of International Application PCT/JP2003/010675, filed Aug. 22, 2003, which claims benefit from Japanese Patent Application No. 2002-247812, filed Aug, 27, 2002, the disclosures of which are incorporated herein by reference in their entireties.

TECHNICAL FIELD

The present invention relates to a novel therapy method relating to direct administration of a biomolecule. More specifically, the present invention is related to administration of a biomolecule using a viral envelope. The present invention also relates to a method for delivering a biomolecule to the brain in an efficient way.

BACKGROUND ART

A number of virus and non-virus methods have been developed to introduce genes into cultured cells or biological tissues for the purposes of gene function analysis, gene therapy, and similar applications (Mulligan, Science, 260, 926 to 932, 1993; and Ledley, Human Gene Therapy, Vol. 6, 1129 to 1144, 1995). Virus methods are most effective for the delivery of genes into cells. However, virus vectors may raise problems due to the co-introduction of gene elements essential for parent genes derived from the parent virus, expression of virus genes, an immunogenicity, and the like. On the other hand, a liposome method, which is a non-virus method, has a lower level of cytotoxicity and immunogenicity than virus methods, but also tends to have a lower level of gene introduction efficiency into biological tissues that that of virus vectors.

Hemagglutinating virus of Japan (HVJ) was first reported as fusing Ehrlich tumor cells (Okada, Biken Journal, 1, 103-110, 1958), then the mechanism of its ability to fuse cell membranes (hereinafter referred to as "fusion activity") was clarified and the possible use of it as a gene introduction vector has been studied. It is known that HVJ has a high level of immunogenicity, and particularly induces Cytotoxic T lymphocyte (CTL) when a large amount of NP protein is produced (Cole G. A. et al., Journal of Immunology, 158, 4301 to 4309, 1997). It is also likely that HVJ inhibits protein synthesis in hosts. To avoid these problems, a technique was devised in which a liposome including a gene or protein is fused with HVJ which has been inactivated by ultraviolet irradiation to prepare a fusion particle (HVJ-liposome) This technique made it possible to introduce a gene non-invasively into cultured cells or organisms (U.S. Pat. No. 5,631,237; Dzau et al., Proc. Natl. Acad. Sci. USA, 93, 11421 to 11425, 1996, and Kaneda et al., Molecular Medicine Today, 5, 298 to 303, 1999). However, the technique requires preparation of two different vehicles, a liposome and a viral envelope, which complicates the technique. The fusion particle of a liposome and HVJ disadvantageously has an average diameter about 1.3 times that of HVJ and a fusion activity one-tenth that of HVJ. In addition, for conventional HVJ-based vectors, there are some tissues in which it is not possible to introduce genes, or if it is possible, it is only possible with very low efficiency.

The present inventors have provided various novel inactivated virus envelope vectors for introducing a gene or oligonucleotide into cultured cells or organisms (WO01/57204). Specifically, by packaging genes into envelopes of various envelope viruses (e.g., HVJ, etc.), whose genomes are previously inactivated, the resultant viruses can be used as vectors capable of introducing genes into cultured cells or biological tissues with simplicity and high efficiency. These viral vectors are also less toxic to cells.

The present inventors have developed a method for producing an inactivated viral envelope at an industrial scale which is inexpensive, effective and secures a good quality product, by employing the use of an alkylating agent.

In the present days, although some treatments exist for many diseases, diseases and disorders of the brain is a field where few solutions are found. Further, demand for such treatment and prevention is increasing very year.

Among encephalopathies, cerebral occlusive disease caused by atherosclerosis of the cerebral arteries or Moyamoya disease, often causes chronic hypoperfusion of the brain. Although such a condition leads not only to cerebral ischemic events, but also to neuropathological changes including dementia (Kalaria R N, Bhatti S U, Lust W D, Perry G., Ann N Y Acad Sci. 1993; 695; 190-3.; Kudo T, Takeda M, Tanimukai S, Nishimura T., Stroke. 1993; 24:259-64; discussion 265.; Kurumatani T, Kudo T, Ikura Y, Takeda M., Stroke. 1998; 29:1058-62.; and Sekhon L H, Morgan M K, Spence I, Weber N C., Stroke. 1994; 25:1022-7), an effective treatment of hypoperfusion has not yet been established.

Recently, preclinical studies have demonstrated that angiogenic growth factors such as vascular endothelial growth factor (VEGF), fibroblast growth factor (FGF), and hepatocyte growth factor (HGF) can stimulate the development of collateral arteries in an animal brain ischemia model (Harrigan M R, Ennis S R, Masada T, Keep R. F., Neurosurgery. 2002; 50:589-98; Lyons M K, Anderson R E, Meyer F B., Brain Res. 1991; 558:315-20.; and Yoshimura S, et al., Hypertension. 2002; 39:1028-34.), a concept called therapeutic angiogenesis. The efficacy of therapeutic angiogenesis using gene transfer of angiogenic growth factors has been reported in human patients with critical limb ischemia or myocardial infarction (Baumgartner I, et al., circulation. 1998; 97:1114-23.; Losordo D W, et al., Circulation. 1998; 98:2800-4.; Symes J F, et al., Ann Thorac Surg. 1999; 68:830-6; discussion 836-7.; and Rosengart T K, et al., Circulation. 1999; 100:468-74.). Accordingly, possible therapeutic angiogenesis should be possible for the treatment of patients with cerebral ischemia, if safe and effective gene transfer methods were developed for human treatment. From this viewpoint, the current gene transfer techniques are not ideal. Gene transfer to the central nervous system (CNS) can be achieved by using various viral vectors including adeno-associated virus (AAV) (Fan D, et al., Neurosci Lett. 1998; 248:61-4), retrovirus (Franceschini I A, et al., J Neurosci Res. 2001; 65:208-19), adenovirus (Miyaguchi K, Maeda Y, Collin C, Sihag R K., Brain Res Bull. 2000; 51:195-202.) and herpes simplex virus 1 (Johnson P A, Yoshida K, Gage F H, Friedmann T., Brain Res Mol Brain Res. 1992; 12:95-102.). These vector systems have advantages and disadvantages for human gene therapy. Although these methods are efficient for in vivo gene transfer into CNS, numerous problems such as safety and production are yet to be resolved toward human gene therapy.

In order to solve these problems, we have developed and used HVJ (Hemagglutinating Virus of Japan =Sendai virus) envelope vector, which is a novel non-viral vector system, as mentioned above. This vector system was developed based on HVJ-based gene transfer of the first generation using a viral envelope and liposome (Yamada K, et al., Am J Physiol. 1996; 271:R1212-20; Kaneda Y, et al., Exp Cell Res. 1987; 173:56-69.) (HVJ liposome methods). The first generation HVJ vector has great potential with regards to transfection to the CNS of rat and primate (Yamada K. et al. ibid; Hagihara Y. et al., Gene Ther. 2000; 7:759-63.). However, there are some deficiencies in that it requires complicated procedure to prepare the vector, and has difficulties in its storage. A HVJ-envelope (HVJ-E) vector, a novel non-viral vector system, merely uses an envelope of HVJ for transfer of a foreign gene.

Problem to be Solved by the Present Invention

As such, there is a demand in the art for a method for efficient delivery of a biomolecule (such as gene introduction) into the brain and the central nervous system (CNS) using a viral envelope both in vitro and in vivo.

Further, the efficacy of delivery of a biomolecule using a viral envelope could be improved. Accordingly, there is a demand in the art for developing a system and a method for highly efficient delivery of a biomolecule using a viral envelope.

The object of the present invention is to provide an improved method for efficient delivery of a biomolecule into the brain and the central nervous system using a viral envelope.

DISCLOSURE OF THE INVENTION

Means for Solving the Problems

As a result of a number of studies, the present inventors have found that the above mentioned problems, may be solved by adding a glycosaminoglycan to a viral envelope system.

The present inventors have also found that by using a viral envelope system after occluding artery of the brain or cervix, a biomolecule can be effectively delivered into the brain by using a viral envelope.

Therefore, the present invention is provided below by way of various embodiments.

(1) A system for introducing a biomolecule into a cell, comprising:
 1) a biomolecule;
 2) a viral envelope; and
 3) a glycosaminoglycan.
(2) The system according to Item 1, wherein the viral envelope is inactivated.
(3) The system according to Item 1, wherein the glycosaminoglycan is heparin.
(4) The system according to Item 1, wherein the molecular weight of the glycosaminoglycan is at least 10,000 Da.
(5) The system according to Item 1, wherein the glycosaminoglycan is comprised at the concentration of at least 50 U/ml.
(6) The system according to Item 3, wherein the molecular weight of heparin is form 12,000 to 15,000 Da.
(7) The system according to Item 3, wherein the degree of sulfation of said heparin is pharmaceutically acceptable.
(8) The system according to Item 1, wherein the viral envelope is an envelope of an RNA virus.
(9) The system according to Item 1, wherein the viral envelope is an envelope of a virus belonging to the *Paramixovirus* genus.
(10) The system according to Item 1, wherein the viral envelope is an envelope of HVJ.
(11) The system according to Item 1, wherein the biomolecule is selected from the group consisting of a nucleic acid, a polypeptide, a lipid, a sugar, and a complex molecule thereof.
(12) The system according to Item 1 wherein the biomolecule comprises a nucleic acid.
(13) The system according to Item 1 wherein the biomolecule comprises a polypeptide.
(14) The system according to Item 1 wherein the biomolecule is a nucleic acid encoding a gene selected from the group consisting of Vascular endothelial growth factor (VEGF), Fibroblast growth factor (FGF), and Hepatocyte growth factor (HGF).
(15) The system according to Item 1 wherein the biomolecule is a polypeptide selected from the group consisting of Vascular endothelial growth factor (VEGF), Fibroblast growth factor (FGF), and Hepatocyte growth factor (HGF).
(16) The system according to Item 3, wherein the heparin, the biomolecule and the viral envelope are contained in a same composition.
(17) The system according to Item 3, wherein the heparin is contained in a different composition from that which comprises the biomolecule and the viral envelope.
(18) The system according to Item 1, wherein the biomolecule is contained in the viral envelope.
(19) A method for introducing a biomolecule into a cell, comprising the steps of:
 A) administering to a cell a composition comprising a viral envelope and a biomolecule; and
 B) administering a glycosaminoglycan to the cell.
(20) The method according to Item 19, wherein the step of administering the glycosaminoglycan is performed simultaneously with the step of administering the composition.
(21) The method according to Item 19, wherein the step of administering the glycosaminoglycan is performed prior to the step of administering the composition.
(22) The method according to Item 19, wherein the step of administering the glycosaminoglycan is performed after the step of administering the composition.
(23) Use of a glycosaminoglycan for manufacturing a medicament for introducing a biomolecule into a cell, wherein the medicament comprises
 A) a biomolecule;
 B) a viral envelope; and
 C) a glycosaminoglycan.
(24) A method for delivering a biomolecule to a brain, comprising the steps of:
 A) transiently occluding an artery of the head portion or cervical portions; and
 B) introducing a biomolecule into the brain during the occluding of the artery of a head portion or a cervical portion.
(25) The method according to Item 24, wherein the biomolecule is selected from the group consisting of a nucleic acid, a polypeptide, a lipid, a sugar, and a complex molecule thereof.
(26) The method according to Item 24, wherein the biomolecule comprises a nucleic acid.
(27) The method according to Item 24, wherein the biomolecule is a nucleic acid encoding a gene selected from the group consisting of Vascular endothelial growth factor (VEGF), Fibroblast growth factor (FGF), and Hepatocyte growth factor (HGF).
(28) The method according to Item 26, wherein the nucleic acid is delivered by a vector.
(29) The method according to Item 24, wherein the biomolecule is introduced with a viral envelope.
(30) The method according to Item 29, wherein the viral envelope is inactivated.
(31) The method according to Item 29, wherein the viral envelope is an envelope of an RNA virus.

(32) The method according to Item 29, wherein the viral envelope is an envelope of a virus belonging to the *Paramixovirus* genus.

(33) The method according to Item 29, wherein the viral envelope is an envelope of HVJ.

(34) The method according to Item 24, wherein the biomolecule is introduced with a glycosaminoglycan.

(35) The method according to Item 34, wherein the glycosaminoglycan is heparin.

(36) The method according to Item 34, wherein the molecular weight of the glycosaminoglycan is at least 10,000 Da.

(37) The method according to Item 34, wherein the glycosaminoglycan is comprised at the concentration of at least 50 U/ml.

(38) The method according to Item 35, wherein the molecular weight of said heparin is from 12,000 to 15,000 Da.

(39) The method according to Item 35, wherein degree of sulfation of said heparin is pharmaceutically acceptable.

(40) The method according to Item 34, wherein the glycosaminoglycan is simultaneously administered with the biomolecule.

(41) The method according to Item 34, wherein the glycosaminoglycan is administered prior to the administration of the biomolecule.

(42) The method according to Item 34, wherein the glycosaminoglycan is administered after the administration of the biomolecule.

(43) The method according to Item 24, wherein the artery of the head portion or the cervical portion is closed for 1 minute to 120 minutes.

(44) The method according to Item 24, wherein the artery of the head portion or the cervical portion is the middle cerebral artery or the carotid artery.

(45) The method according to Item 24, wherein the artery of the head portion or the cervical portion is the middle cerebral artery.

(46) The method according to Item 24, wherein the biomolecule is administered into a carotid artery, on a thalamus, intracerebroventricularly or intrathecally.

(47) The method according to Item 24, wherein the biomolecule is administered into the carotid artery.

(48) A kit for delivering a biomolecule into a brain, comprising:
   A) a biomolecule; and
   B) an instruction indicating a method for administering the biomolecule, wherein the method comprises:
      a) transiently occluding an artery of a head portion or a cervical portion; and
      b) introducing the biomolecule into the brain during the occluding of the artery of the head portion or the cervical portion.

(49) The kit according to Item 48, wherein the biomolecule is selected from the group consisting of a nucleic acid, a polypeptide, a lipid, a sugar, and a complex molecule thereof.

(50) The kit according to Item 48, wherein the biomolecule comprises a nucleic acid.

(51) The kit according to Item 48, wherein the biomolecule is a nucleic acid encoding a gene selected from the group consisting of Vascular endothelial growth factor (VEGF), Fibroblast growth factor (FGF), and Hepatocyte growth factor (HGF).

(52) The kit according to Item 48, wherein the nucleic acid is delivered by a vector.

(53) The kit according to Item 48, further comprising a viral envelope.

(54) The kit according to Item 53, wherein the viral envelope is inactivated.

(55) The kit according to Item 53, wherein the viral envelope is an envelope of an RNA virus.

(56) The kit according to Item 53, wherein the viral envelope is an envelope of a virus belonging to the *Paramixovirus*- genus.

(57) The kit according to Item 53, wherein the viral envelope is an envelope of HVJ.

(58) The kit according to Item 48, further comprising a glycosaminoglycan.

(59) The kit according to Item 58, wherein the glycosaminoglycan is heparin.

(60) The kit according to Item 58, wherein the molecular weight of the glycosaminoglycan is at least 10,000 Da.

(61) The kit according to Item 58, wherein the glycosaminoglycan is comprised at the concentration of at least 50 U/ml.

(62) The kit according to Item 59, wherein the molecular weight of the heparin is from 12,000 to 15,000 Da.

(63) The kit according to Item 59, wherein the degree of sulfation of said heparin is pharmaceutically acceptable.

(64) The kit according to Item 58, wherein the glycosaminoglycan is simultaneously administered with the biomolecule.

(65) The kit according to Item 58, wherein the glycosaminoglycan is administered prior to the administration of the biomolecule.

(66) The kit according to Item 58, wherein the glycosaminoglycan is administered after the administration of the biomolecule.

(67) The kit according to Item 48, wherein the artery of the head portion or the cervical portion is closed for 1 minute to 120 minutes,

(68) The kit according to Item 48, wherein the artery of the head portion or the cervical portion is the middle cerebral artery or the carotid artery.

(69) The kit according to Item 48, wherein the artery of the head portion or the cervical portion is the middle cerebral artery.

(70) The kit according to Item 48, wherein the biomolecule is administered into the carotid artery, the thalamus, intracerebroventricularly or intrathecally.

(71) The kit according to Item 48, wherein the biomolecule is administered into the carotid artery.

(72) Use of a biomolecule for manufacturing a kit for delivering the biomolecule into a brain, the kit comprising:
   A) the biomolecule; and
   B) an instruction indicating a method for administering the biomolecule, wherein the method comprises:
      a) transiently occluding an artery of a head portion or a cervical portion; and
      b) introducing the biomolecule into the brain during the occluding of the artery of the head portion or the cervical portion.

It is to be understood that the advantages and effects of the present invention will become apparent to those skilled in the art upon reading and understanding the description of the present specification.

BRIEF DESCRIPTION OF THE DRAWINGS

This application file contains at least one drawing executed in color. Copies of this patent or patent application publication with color drawings will be provided by the U.S. Patent and Trademark Office upon request and payment of the necessary fee.

DETAILED DESCRIPTION OF THE INVENTION

Figure 1:
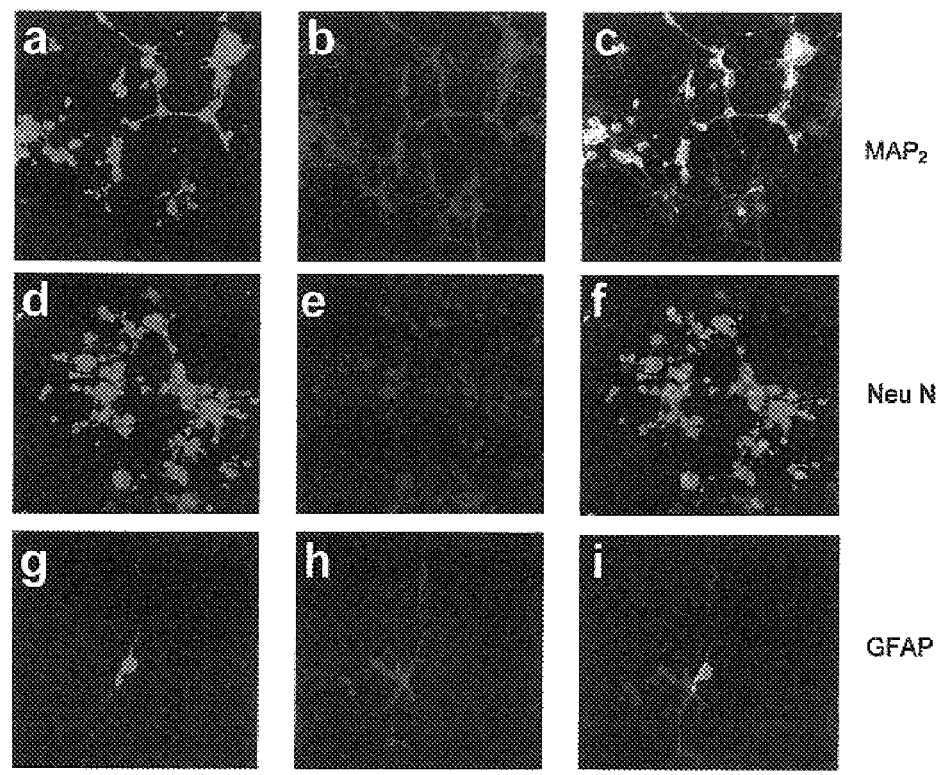
FIG. 1. Typical example of the cultured rat cerebral cortex neurons and glial cells transfected with Venus gene using HVJ-E vector. Laser scanning confocal microscopy images of Venus (a, d, g), immunofluorescent staining for $MAP_2$ (b), NeuN (e), GFAP (h), and merged images (c, f, i). Most of the cells expressing Venus were immuno-positive for $Map_2$ and NeuN (a-f). This experiment was repeated at least five times.

Hereinafter the present invention is described. It should be understood throughout the present specification that the singular forms include plural referents unless the context clearly dictates otherwise. It should also be understood that the terms as used herein have definitions typically used in the art unless otherwise mentioned.

Terms specifically used herein will be described below.

As used herein, the term "virus" refers to a transmissible small structure which has DNA or RNA as its genome and proliferates only within infected cells. Viruses include a virus belonging to a family selected from the group consisting of the family Retroviridae, the family Togaviridae, the family Coronaviridae, the family Flaviviridae, the family Paramyxoviridae, the family Orthomyxoviridae, the family Bunyaviridae, the family Rhabdoviridae, the family Poxyiridae, the family Herpesviridae, the family Baculoviridarie, and the family Hepadnaviridae. A virus used herein may be preferably influenza virus or Sendai virus of the family Orthomyxoviridae. More preferably, a virus used herein is Sendai virus.

As used herein, the terms "Sendai virus" or "HVJ" (Hemagglutinating virus of Japan) are used interchangeably, referring to a virus capable of cell fusion of the genus paramyxovirus of the family paramyxovirus. M. Kuroya et al. reported Sendai virus (1953). The genome is a minus strand of RNA having a base length of about 15,500. The particle of Sendai virus comprises an envelope and has a diameter of 150 nm to 300 nm (polymorphism). Sendai virus has RNA polymerase. The virus is unstable to heat, and causes hemolysis and agglutination of substantially all types of red blood cells. The virus grows in the cytoplasm of developing chicken eggs and/or cultured cells derived from the kidney of various animals. When established cells are infected with Sendai virus, persistent infection is likely to occur. The virus has the ability to fuse various cells, and therefore, is widely used in the formation of heterokaryons, preparation of hybrid cells, and the like.

As used herein, the term "(virus or viral) envelope" refers to a membrane structure which basically comprises a lipid bilayer surrounding a nucleocapsid which exists in specific viruses such as Sendai virus and the like. Envelopes are typically observed in mature viruses budding from cells. An envelope generally consists of host-derived lipids and small projecting structures consisting of spike proteins encoded by viral genes. Therefore "(viral) envelope vector" is a designation when using the envelope as a vector, and as used herein it can be interchangeably used with "viral envelope", when appropriate.

As used herein the term "glycosaminoglycan" refers to a polysaccharide in which the main component is hexosamine. Such a glycosaminoglycan includes but is not limited to hyaluronic acid, chondroitin sulfate, dermatan sulfate, keratan sulfate, heparan sulfate, heparin and a mixture thereof. As used herein "hexosamine" refers to a hexose in which a hydroxy group is replaced with an amino acid group. Glycosaminoglycan is usually classified as described above, however, it has been reported that there are some molecules which are difficult to be definitively classified, such as a molecule a part of which has a chondroitin sulfate structure, and another part has a dermatin sulfate structure and the like. Except for hyaluronic acids, which are synthesized and secreted by Streptococcus(Group A), almost all glycosaminoglycans are side chain components of a proteoglycan produced by an animal cell (mainly cells of connective tissue), and can be obtained by enzymatically processing core protein portions thereof, or by digesting the binding between the protein and the side chain of glycosaminoglycan by alkaline processing, in the case of ester type in which the glycosaminoglycan is bound to a serine or a threonine of the protein. The anionic structure with high molecular weight of glycosaminoglycan is useful for comprising a number of water molecules. As used herein, glycosaminoglycans include both glucosaminoglycan and galactosaminoglycan. Galactosaminoglycans refer to glycosaminoglycan including galactosamine, and include, for example, chondroitin sulfate, dermatan sulfate, and the like. Glucosaminoglycans refer to a glycosaminoglycan including glycosamine, and include, for example, heparin, heparan sulfate and the like.

As used herein, the term "heparin" refers to a glycosaminoglycan essentially consisting of D-glycosamine and D-glucuronic acid (for example, polymerized in an alternate manner). Sulfate is bound to the 2,6-amino group of almost all glucosamine, as well as to the hydroxy group at the position 6 thereof, and the position 2 of uronic acid. Heparin that is synthesized in mast cells of an animal, and has a number of sulfate and carboxyl groups, thus it is a negatively charged electrolyte with high molecular weight. It has an inhibitory activity of blood coagulation.

As used herein the term "sulfation" refers to replacement of substituent (for example, amino group, hydroxy group and the like) with a sulfate group, The degree of sulfation is an important factor determining the degree of charge of a molecule, and it is believed that change in the strength of the cellular membrane surface can affect the efficiency of delivery of a viral envelope in the present invention. Accordingly, in a preferable embodiment, the degree of sulfation used is pharmaceutically acceptable.

The term "biomolecule" as used herein refers to a molecule related to an organism. An "organism (or "bio-")" as used herein refers to a biological organic body, including, but being limited to, an animal, a plant, a fungus, a virus, and the like, A biomolecule includes a molecule extracted from an organism, but is not so limited. A biomolecule is any molecule capable of having an influence on an organism. Therefore, a biomolecule also includes a molecule synthesized, for example, by combinatorial chemistry, and a low weight molecule capable of being used as a medicament (e.g., a low molecular weight ligand, etc.) as long as they are intended to have an influence on an organism. Examples of such biomolecules include, but are not limited to, proteins, polypeptides, oligopeptides, peptides, polynucleotides, oligonucleotides, nucleotides, nucleic acids (e.g., including DNA (such as cDNA and genomic DNA) and RNA (such as mRNA)), polysaccharides, oligosaccharides, lipids, low weight molecules (e.g., hormones, ligands, signal transduction substances, low-weight organic molecules, etc.), and complex molecules thereof, and the like. A biomolecule also includes a call itself, and a part or the whole of tissue, and the like as long as they can be coupled to a substrate of the present invention. Preferably, a biomolecule includes a nucleic acid or a protein. In a preferable embodiment, a biomolecule is a nucleic acid (e.g., genomic DNA or cDNA, or DNA synthesized by PCR or the like). In another preferable embodiment, a biomolecule may be a protein.

As used herein, the term "biological activity" refers to the activity which a certain factor (e.g., virus, polynucleotide or polypeptide) has within an organism, including activity exhibiting various functions. For example, when the certain factor is a transcriptional factor, its biological activity includes activity to regulate transcriptional activity. When the certain factor is a virus, its biological activity includes infection activity. As another example, when the certain factor is a ligand, its biological activity includes binding to a receptor to which the ligand corresponds. Such biological activity can be "inactivated".

As used herein, the term "inactivation" in relation to a virus (e.g., Sendai virus, etc.) indicates that the genome of the virus is inactivated. The inactivated virus is incapable of replication. Inactivation is achieved by a method described herein such as alkylation and the like. Such a method for inactivation includes but is not limited to a method comprising the steps of: (a) inactivating a virus (e.g., HVJ, etc.) with an alkylating agent; (b) obtaining a condensate solution of the virus or the inactivated virus; and (c) purifying the virus or the inactivated virus by column chromatography and then ultrafiltration, and a method comprising the same steps but the order thereof being rearranged.

As used herein, the term "alkylation" refers to an action which substitutes an alkyl group for a hydrogen atom of an organic compound. The term "alkylating agent" refers to a compound which supplies an alkyl group. Examples of alkylating agents include, but are not limited to, organic metal compounds such as alkyl halide, dialkyl sulfate, alkyl sulfonate, alkyl lead, and the like. Examples of preferable alkylating agents include, but are not limited to, β-propiolactone, butyrolactone, methyl iodide, ethyl iodide, propyl iodide, methyl bromide, ethyl bromide, propyl bromide, dimethyl sulfate, diethyl sulfate, and the like.

As used herein, "nucleic acid", "nucleic acid molecule", "polynucleotide", and "oligonucleotide" are herein used interchangeably to refer to macromolecules (polymer) comprising a series of nucleotides, unless otherwise specified. A nucleotide refers to a nucleoside whose base is a phosphoric ester. The base of the nucleotide is a pyrimidine or purine base (pyrimidine nucleotide and purine nucleotide). Polynucleotides include DNA or RNA.

As used herein, "nucleotide" refers to any naturally occurring nucleotide and non-naturally occurring nucleotide. "Derived nucleotide" refers to a nucleotide which is different from naturally occurring nucleotides but has a function similar to that of its original naturally occurring form. Such derived nucleotides are well known in the art.

As used herein, the term "fragment" in relation to a nucleic acid molecule refers to a polynucleotide whose length is shorter than the full length of the reference nucleic acid molecule, but is sufficient as an agent of the present invention. Therefore, the term "fragment" refers to a polynucleotide which has a sequence length ranging from 1 to n−1 with respect to the full length of the reference polynucleotide (of length n). The length of the fragment can be appropriately changed depending on the purpose. For example, the lower limit of the length of the fragment includes 5, 6, 7, 8, 9, 10, 15, 20, 25, 30, 40, 50, 75, 100 or more nucleotides. Lengths represented by integers which are not herein specified (e.g., 11 and the like) may be appropriate as a lower limit. Homology may be represented by a score measured by a search program BLAST using an algorithm developed by Altschul et al. (J. Mol. Biol., 215, 403-410 (1990)).

As used herein, the terms "protein", "polypeptide", and "peptide" are used interchangeably, referring to a macromolecule which consists of a series of amino acids. The term "amino acid" refers to an organic molecule which has a carboxyl group and an amino group bound to a carbon atom. Preferably, amino acids herein include, but are not limited to, 20 naturally occurring amino acids.

As used herein, the term "gene" refers to an element defining a genetic trait. A gene is typically arranged in a given sequence on a chromosome. A gene which defines the primary structure of a protein is called a structural gene. A gene which regulates the expression of a structural gene is called a regulatory gene. As used herein, the term "gene" may refer to "polynucleotide", "oligonucleotide", "nucleic acid", and "nucleic acid molecule" and/or "protein", "polypeptide", "oligopeptide" and "peptide".

As used herein the term "foreign gene" refers to a nucleic acid sequence to be included in a gene introduction vector derived from a source other than viral sequence. In one aspect of the invention, the foreign gene is operably linked to an appropriate sequence (for example, promoter, enhancer, terminator, and poly A signal necessary for transcription, and ribosome binding site, start codon, termination codon necessary for translation, and the like) in order to express the gene introduced by a gene introduction vector. In another aspect, the foreign gene does not include a regulatory sequence for expressing the foreign gene. In a further aspect, the foreign gene is an oligonucleotide or decoy nucleic acid.

As used herein the term "gone library" refers to a nucleic acid library, including a naturally isolated nucleic acid sequence, or a synthetic nucleic acid sequence. Sources of naturally isolated nucleic acids include, but are not limited to, genomic sequences from eukaryotic cells, prokaryotic cells or viruses, or cDNA sequences. A library in which an arbitral sequence (for example, signal, tag sequences or the like) is added to a naturally isolated sequence is also included in the definition of a gene library of the present invention. In one embodiment, the gene library includes sequences rendering transcription and/or translation of the nucleic acid such as the promoter and the like.

As used herein, the term "screening" refers to selection or an assay of members having a desired activity or function from a library such as a gene library. Such a method of screening is known in the art.

As used herein, the term "gene introduction" refers to introduction of a desired, natural, synthetic or recombinant gene or gene fragment into a target cell in vivo or in vitro in such a manner that the function of the introduced gene is maintained. The gene or gene fragment to be introduced in the present invention includes DNA, RNA having a specific sequence, or a synthetic analog thereof. Further, as used herein, gene introduction is used interchangeably with the terms "transfection" and "transfect".

As used herein "gene introduction activity" refers to the activity of "gene introduction" by a vector, and can be detected by the function of the gene introduced (for example, when using an expression vector, expression and/or activity of a protein encoded thereby).

As used herein, the term "expression" of a polynucleotide, a polypeptide, or the like, indicates that the gene or the like is affected by a predetermined action in vivo to be changed into another form. Preferably, the term "expression" indicates that a gene, a polynucleotide, or the like is transcribed and translated into a polypeptide. In addition, generation of mRNA via transcription may be an aspect of the "expression". More preferably, such a polypeptide may have a form modified by post-translational processing. As used herein, the term "regulation" in relation to the expression of a gene refers to, but is not limited to, enhancement, reduction, induction, elimination, deceleration, acceleration, and the like of gene expression.

Examples of a gene to be treated include, but are not limited to, genes encoding enzymes, hormones, lymphokines, receptors, growth factors, regulatory proteins, polypeptides affecting the immune system, immunoregulatory factors, antibodies, and the like. Specifically, these genes include, but are not limited to, genes encoding human growth hormones, insulin, interleukin-2, tumor necrosis factors, nerve growth factors (NGFs), epithelial growth factors, tissue plasminogen activators (TPAs), Factor VIII:C, calcitonin, thymidine kinase, interferon, granulocyte-macrophage colony-stimulating factors (GMCSFs), erythropoietin (EPO), hepatocyte growth factors (HGFs), and the like. These genes may be present in the form of a nucleic acid or a polypeptide in a medicament of the present invention.

As used, herein the term "vector", when referring to a gene, refers to those capable of transferring a polynucleotide sequence of interest to a cell of interest. Examples of such vector include one capable of autonomous replication in a host cell such as in an individual animal, or one having a promoter at an appropriate site for transcription of the polynucleotide of the present invention which is capable of being incorporated in the chromosome of the host. As used herein, the vector may be a plasmid.

As used herein, the term "expression vector" refers to a nucleic acid sequence in which a structural gene, a promoter regulating the expression thereof, and a variety of regulatory elements are operably linked in the host cell. Such regulatory elements preferably may include terminators, selective marker such as drug resistant genes, and enhancers. It is well known to those skilled in the art that the types of expression vectors of organisms such as animals, and species of regulatory elements to be used therein may vary depending on the host cell or organism used. In the case of a human, the expression vector to be used in the present invention, may include pCAGGS (Niwa H. et al., Gene; 108: 193-9(1991)).

As used herein the term "recombinant vector" refers to vectors capable of transferring a polynucleotide sequence of interest to a cell of interest. Examples of such vectors include one capable of autonomous replication, or of being incorporated in to chromosome in a host cell such as in an individual animal and having a promoter at an appropriate site for transcription of the polynucleotide of the present invention.

Examples of "recombinant vectors" for animal cells include, but are not limited to, pcDNAI/Amp, pcDNAI, pCDM8 (all commercially available from Funakoshi), pAGE107 [Japanese Laid-Open Publication No. 3-229, 79, Cytotechnology, 3, 133 (1990), pREP4 (Invitrogen), pAGE103 [J. Biochem., 101, 1307(1987)], pAMo, pAMoA [J. Biol. Chem., 268, 22782-22787(1993)], pCAGGS (Niwa, H., et al., Gene; 108, 193-199 (1991), and the like.

As used herein, the term "terminator" refers to a sequence which is located downstream of a protein-encoding region in a gene and which is involved in the addition of a poly-A sequence and the termination of transcription when DNA is transcribed into mRNA. It is known that a terminator contributes to the stability of mRNA and has influence on the amount of gene expression. Terminators include, but are not limited to, those from a mammal, as well as CaMV35S terminator, nopaline synthase gene terminator (Tnos), tobacco PR1a gene terminator, and the like.

As used herein, the term "promoter" refers to a base sequence which determines the initiation site of transcription of a gene and is a region located in DNA which directly regulates the frequency of transcription Transcription is started by RNA polymerase binding to a promoter. Accordingly, a portion of a gene having promoter function herein refers to "promoter moiety". A promoter region is usually located within about 2 kbp upstream of the first exon of a putative protein coding region. Therefore, it is possible to estimate a promoter region by predicting a protein coding region in a genomic base sequence using DNA analysis software. A putative promoter region is usually located upstream of a structural gene, but depending on the structural gene, a putative promoter region may be located downstream of a structural gene. Preferably, a putative promoter region is located within about 2 kbp upstream of the translation initiation site of the first exon.

As used herein when referring to expression of a gene, the term "site specificity" generally refers to specificity of expression of the gene in a site (for example, in the case of an animal, the heart, myocardiac cell and the like) of an organism (for example, an animal). The term "time specificity" refers to specificity of expression of a gene depending on a specific stage (for example, at the time of stroke and the like) of an organism (for example, an animal).

Examples of a vaccine which may be herein used as a medicament include, but are not limited to, vaccines for cancer, acquired immunodeficiency syndrome, measles, herpes simplex, and the like. These vaccines may be present in the form of a nucleic acid or a peptide in a medicament of the present invention.

The present invention provides a pharmaceutical composition or a medicament comprising the above-described envelope singly or in combination with a stabilizing compound, a diluent, a carrier, or other ingredients and pharmaceutical agents. Preferably, the present invention may be in the form of a vaccine or in other forms suitable for gene therapy.

A pharmaceutical composition and medicament of the present invention may be used in a form which allows the envelope thereof to be taken into cells at an affected site or cells of a tissue of interest.

A pharmaceutical composition and medicament of the present invention may be administered within any aseptic biocompatible pharmaceutical carrier including, but not being limited to, physiological saline, buffered physiological saline, dextrose, water, and the like. Any of these molecules may be administered into patients within a pharmaceutical composition, which is mixed with an appropriate excipient, adjuvant, and/or pharmaceutically acceptable carrier, singly or in combination with other pharmaceutical agents. In a certain embodiment of the present invention, a pharmaceutically acceptable carrier is pharmaceutically inactive.

A pharmaceutical composition and medicament of the present invention is administered orally or parenterally. Examples of parenteral delivery methods include, but are not limited to, topical, intraarterial (e.g., via the carotid artery, or the like), intramusclar, subcutaneous, intramedullary, subarachnoideal, intraventicular, intravenous, intraperitoneal, and intranasal administrations, and the like. In the present invention, any route which allows delivery to a site to be treated may be used.

As used herein, the term "head portion" refers to a portion of the body, including cranial bone, the content thereof, and related structures. As used herein "head portion" includes a brain.

As used herein, the term "cervical portion" refers to regions between the head portion and the upper extremity. As used herein, the head-cervical (head and neck) portion or craniocervical portion may refer to the neck and above portions.

As used herein the term "transiently" refers to that when a treatment has taken place, such a treatment is continued for a certain period of time. Accordingly, after the treatment ceases, effects of the treatment will be lost or diminished.

As used herein the term "artery" refers to a blood vessel delivering blood from the heart to each portion of the body. Accordingly, the term "cerebral artery" refers to an artery present in the brain.

As used herein the term to "occlude" an artery or a blood vessel refers to treat, the same so that a blood stream is significantly reduced or stopped compared to when the treatment is not performed. Preferably, it is preferable not to cause hemorrhage when an occlusion is performed. Means for occluding an artery or a blood vessel include, but are not limited to, balloon catheter, clipping and the like.

As used herein "introducing" a biomolecule into a space (for example, "into a cell (intracellularly)") refers to the transfer of such a biomolecule from a different space to the space of interest. Such an introduction may use any means, and may be active introduction or passive introduction.

As used herein the term "system" refers to a product consisting of a plurality of components, including pharmaceuticals, agricultural chemicals, compositions (for example, pharmaceutical compositions), vaccines, kit and the like.

In addition to an envelope, these pharmaceutical compositions and pharmaceutical agents may comprise a pharmaceutically acceptable carrier containing other compounds for promoting processing of the envelope in order to prepare an excipient or pharmaceutically acceptable composition. Further details of prescription and administration are described in, for example, the latest edition of Japanese Pharmacopeia and its latest supplement, the latest edition of "REMINGTON'S PHARMACEUTICAL SCIENCES" (Maack Publishing Co., Easton, Pa.), or the like.

A pharmaceutical composition for oral administration may be prepared using a pharmaceutically acceptable carrier well known in the art in a form suitable for administration. Such a carrier can be prepared as a tablet, a pill, a sugar-coated agent, a capsule, a liquid, a gel, a syrup, a slurry, a suspension, or the like, with which it is suited for the patient to take the pharmaceutical composition.

The pharmaceutical composition for oral use may be obtained in the following manner: an active compound is combined with a solid excipient, the resultant mixture is pulverized if necessary, an appropriate compound is further added if necessary to obtain a tablet or the core of a sugar-coated agent, and the granular mixture is processed. The appropriate excipient may be a carbohydrate or protein filler, including, but not being limited to, the following: sugar including lactase; sucrose, mannitol, or sorbitol; starch derived from maize, wheat, rice, potato, or other plants, cellulose such as methylcellulose, hydroxypropylmethylcellulose, or sodium carboxymethylcellulose; and gum including gum Arabic and gum tragacanth; and proteins such as gelatin and collagen. A disintegrant or a solubilizing agent such as crosslinked polyvinyl pyrrolidone, agar, alginic acid or a salt thereof (e.g., sodium alginate) may be used if necessary.

The sugar-coated agent core is provided along with an appropriate coating, such as a condensed sugar solution. The sugarcoated agent core may also contain gum arabic, talc, polyvinyl pyrrolidone, carbopolygel, polyethylene glycol, and/or titanium dioxide, a lacquer solution, and an appropriate organic solvent or a mixed solvent solution. To identify a product, or characterize the amount of an active compound (i.e., dose), dye or pigment may be added to tablets or sugar-coated agents.

The pharmaceutical composition which may be orally used may contain, for example, a soft sealed capsule consisting of a gelatin capsule, gelatin and coating (e.g., glycerol or sorbitol). The gelatin capsule may contain an active ingredient mixed with a filler or binder such as lactose or starch, a lubricant such as talc or magnesium stearate, and optionally a stabilizer. In the soft capsules the decoy compound may be dissolved or suspended in an appropriate liquid, such as fatty oil, liquid paraffin or liquid polyethylene glycol, with or without a stabilizer.

The pharmaceutical composition for parenteral administration contains an aqueous solution of an active compound. For the purpose of injection, the pharmaceutical composition of the present invention is prepared in an aqueous solution, preferably Hank's solution, Ringer's solution, or a physiologically suitable buffer such as a buffered physiological saline. The aqueous suspension for injection may contain a substance for increasing the viscosity of a suspension (e.g., sodium-carboxymethylcellulose, sorbitol, or dextran). Further, the suspension of the active compound may be prepared as an appropriate oily suspension. Appropriate lipophilic solvents or vehicles include fatty acids such as sesame oil, synthetic fatty acid esters such as ethyl oleate or triglycerides, or liposomes. The suspension may contain a stabilizer which allows a high-concentration solution preparation, or an appropriate pharmaceutical agent or reagent for increasing the solubility of the compound, if necessary.

The pharmaceutical composition of the present invention may be produced using a process similar to processes known in the art (e.g., conventional mixing, dissolution, rendering to granules, preparation of a sugar-coated agent, elutriation, emulsification, capsulation, inclusion, or freeze drying).

A pharmaceutical composition of the present invention includes a composition containing an effective amount of an envelope of the present invention which can achieve the intended purpose of the decoy compound. "Therapeutically effective amount" and "pharmacologically effective amount" are terms which are well recognized by those skilled in the art and which refer to an amount of pharmaceutical agent effective for production of an intended pharmacological effect. Therefore, therapeutically effective amount is an amount sufficient for reducing the manifestation of the disease to be treated. A useful assay for confirming an effective amount (e.g., a therapeutically effective amount) for a predetermined application is to measure the degree of recovery from a target disease. The amount actually administered depends on the individual to be treated. The amount is preferably optimized so as to achieve a desired effect without significant side effects. The determination of therapeutically effective dose is within the ability of those skilled in the art.

A therapeutically effective dose of any compound can be initially estimated using either a cell culture assay or any appropriate animal model. The animal model is used to achieve a desired concentration range and an administration route. Thereafter, such information can be used to determine a dose and route useful for administration into humans.

The term "therapeutically effective amount" in relation to an envelope refers to an amount which results in amelioration of symptoms or conditions of a disease. Therapeutic effect and toxicity of an envelope may be determined by standard pharmaceutical procedures in cell cultures or experimental animals (e.g., $ED_{50}$, a dose therapeutically effective for 50% of a population; and $LD_{50}$, a dose lethal to 50% of a population). The dose ratio between therapeutic and toxic effects is therapeutic index, and it can be expressed as the ratio of $ED_{50}/LD_{50}$. Pharmaceutical compositions which exhibit high therapeutic indices are preferable. The data obtained from cell culture assays and animal studies can be used in formulating a dosage range for use in humans. The dosage of such compounds-preferably lies within a range of circulating concentrations that include the $ED_{50}$ but have little or no toxicity. Such a dosage may vary within this range depending upon the dosage form employed, the susceptibility of the patient, and the route of administration. As an example, the dose of an envelope is appropriately selected depending on the age and other conditions of a patient, the type of a disease, the type of the envelope employed, and the like.

When an envelope vector of the present invention is administered into a human, from 400 HAU to 400,000 HAU of the envelope vector may be administered per subject, preferably 1,200 HAU to 120,000 HAD, and more preferably 4,000 HAU to 40,000 HAU. The amount of an exogenous gene contained in an envelope to be administered may be from 2 μg to 2,000 μg per subject, preferably from 6 μg to 600 μg per subject, and more preferably from 20 μg to 200 μg.

As used herein, the term "HAU" refers to an amount of viral activity capable of agglutinating 0.5% of chicken red blood cells. 1 HAU corresponds to 24,000,000 virus particles (Okada Y. et al., Biken Journal, 4, 209-213, 1961). The above-described amount can be administered, for example, from once per day to several times per day.

An exact dose may be selected by an individual practitioner in consideration of the patient to be treated. Doses and administration are adjusted to provide a sufficient level of activity or to maintain a desired effect. Further factors to be considered include severity of a disease state (for example, size and position of a tumor; age, bodily weight and sex of a patient; diet regulation; period of time and frequency of administration; combination of drugs; response sensitivity; and resistant/response to the treatment). Depending on the half-life of a specific formulation and clearance rate thereof, sustained-release pharmaceutical compositions may be administered once per three to four days, weekly or bi-weekly. Guidance as to a specific dose and mode of delivery are provided in references known in the art.

The present invention may also comprise a biocompatible material as a composition and medicament. The biocompatible material may comprise at least one selected from the group consisting of silicone, collagen, gelatin, glycolic acid/lactic acid copolymer ethylene/vinyl acetate copolymer, polyurethane, polyethylene, polytetrafluoroethylene, polypropylene, polyacrylate, and polymethacrylate. Silicone is preferable because it is easy to mold. Examples of biodegradable macromolecules include, but are not limited to, polymers, copolymers or mixtures thereof, which are synthesized by noncatalyzed hydration of at least one selected from the group consisting of collagen, gelatin, α-hydroxycarboxylic acids (e.g., glycolic acid, lactic acid, hydroxybutyric acid, etc.); hydroxydicarboxylic acids (e.g., malic acid, etc.), and hydroxytricarboxylic acids (e.g., citric acid, etc.); polyacid anhydrides (e.g., poly-α-cyanoacrylic ester, polyamino acid (e.g., poly-γ-benzyl-L-glutamic acid, etc.); maleic anhydride-based copolymers (e.g., styrene/maleic acid copolymer, etc.); and the like. The manner of polymerization may be any of random, block, and graft polmerization. When α-hydroxycarboxylic acids, hydroxydicarboxylic acids, or hydroxytricarboxylic acids have an optically active center within a molecule, any of D-isomers, L-isomers, and DL-isomers can be used. Preferably, glycolic acid/lactic acid copolymers may be used.

The composition and medicament of the present invention may be provided in a sustained-release form. Any sustained-released dosage form may be used in the present invention. Examples of sustained-release dosage forms include, but are not limited to, rod-like formulations (e.g., pellet-like, cylinder-like, needlelike formulations, etc.), tablet formulations, disk-like formulations, sphere-like formulations, sheet-like formulations, and the like. Methods for preparing sustained-release dosage forms are well known in the art, as described in, for example, the Japanese Pharmacopeia, the U.S. Pharmacopeia, Pharmacopeias of other countries, and the like. Examples of a method for producing sustained-release drugs include, but are not limited to, a method using disaggregation of a drug from a complex, a method for preparing an aqueous suspension of liquid drug, a method for preparing an oil injection solution or oil suspended injection solution, a method for preparing an emulsified injection solution (o/w or w/o type emulsified injection solution, or the like), and the like.

The use of the composition and medicament of the present invention is usually performed under the supervision of a doctor, or without supervision of, a doctor if approved by the authorities and laws of a country in which the present invention is used.

The present invention may also be provided in the form of a vaccine. A vaccine means an antigen in any of various forms (e.g., protein, DNA, and the like) which is used to prevent (or treat) a certain type of disease (e.g., contagious diseases, infectious diseases, and the like). Attenuated live pathogens (live vaccine), inactive pathogens (or a part thereof), metabolites of a pathogen (toxin, inactivated toxin (i.e., toxoid), or the like), DNA vaccines, or the like are used depending on the type of infection, transmission, epidemic, or the like. Vaccination cause the active development of immunity (humoral immunity, cell-mediated immunity, or both) within the body of organisms (humans, livestock, and vectors) and prevents infection, transmission, epidemic, or the like caused by pathogens.

The vaccines of the present invention are not particularly limited to any dosage form, and are prepared in accordance with methods known in the art. Further, the vaccines of the present invention may be in the form of an emulsion containing various adjuvants. The adjuvants aid sustenance of a high level of immunity when the above-described HSV gene recombinant is used in a smaller dose than when it is used alone. Examples of the adjuvants include Freund's adjuvant (complete or incomplete), adjuvant 65 (including peanut oil, mannide monooleate and aluminum monostearate), and aluminum hydrate, aluminum phosphate or mineral gel such as alum. For vaccines for humans, or animals used as a food source, adjuvant 65 is preferable. For vaccines for commercial animals, mineral gel is preferable.

In addition to the above-described adjuvants, the vaccines of the present invention may contain one or more additives for preparation selected from diluents, aroma chemicals, preservatives, excipients, disintegrants, lubricants, binders, surfactants, plasticizers, and the like.

The administration routes of the vaccines of the present invention are not particularly limited, but parenteral administration is preferred. For example, the vaccines are administered parenterally (e.g., intravenously, intraarterially, subcutaneously, intradermal, intramuscularly or intraperitoneally). Preferably, the vaccine of the present invention may be administered via the carotid.

The dose of the vaccines of the present invention can be selected depending on various conditions: what administration is intended; whether infection is primary or recurrent; the age and weight; conditions of patients; the severity of disease; and the like. When intended to treat diseases caused by recurrent infection, the dose of the vaccines of the present invention is preferably about 0.01 ng to 10 mg per kg body weight, and more preferably about 0.1 ng to 1 mg per kg body weight.

The number of administrations of the vaccines of the present invention varies depending on the above-described conditions, and is not necessarily determined in the same manner. However, preferably, the vaccines are repeatedly administered at intervals of days or weeks. Particularly, administration is conducted at several times, or preferably about one to two times, at the interval of about 2 to 4 weeks. The number of administrations (administration time) is preferably determined by symptomatology or a fundamental test using antibody titer while monitoring the conditions of the disease.

Compositions (e.g., vaccines) are herein provided for treating or preventing pathogen infections (e.g., viruses (e.g., HIV, influenza virus, rotavirus, and the like), or bacteria). Such compositions comprise at least one gene or protein of the pathogen. The exogenous gene preferably is full length but may be a partial sequence as long as it contains at least an epitope capable of triggering immunity. The term "epitope" as used herein refers to an antigenic determinant whose structure has been revealed. A method for determining an epitope is known in the art. Once the primary nucleic acid or amino acid sequence of a protein is provided, such epitopes can be determined by such a known routine technique. A useful epitope may have at least a length of three amino acids, preferably, at least 4 amino acids, at least 5 amino acids, at least 6 amino acids, at least 7 amino acids, at least 8 amino acids, at least 9 amino acids, at least 10 amino acids, at least 15 amino acids, at least 20 amino acids, or at least 25 amino acids.

As used herein, the term "neutralizing antibody" refers to an antibody which is involved in a reaction which neutralizes the biological activity of an antigen, such as an enzyme, a toxin, a bacterium, a virus, or the like. The term "neutralizing reaction" refers to a reaction in which an antigen is bound to a neutralizing antibody, so that the activity of the antigen and the antibody is eliminated or lowered. If a vaccine is administered, a neutralizing antibody is produced and serves to get rid of pathogens.

As used herein, the term "gene therapy" or "gene therapeutic method" refers to a method for treating diseases caused by a damaged (or defective) gene by introducing a healthy or modified nucleic acid (e.g., DNA) to patients. Some gene therapies use the step of injecting a naked nucleic acid, though vectors are often used. A virus envelope of the present invention may be used as such a vector.

The present invention may be provided in the form of a kit comprising a composition and medicament. The kit comprises a composition and medicament of the present invention, and instructions which provide guidance in administering the composition and medicament. The instructions describe a statement indicating an appropriate method for administering a composition or a medicament of the present invention. The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are a so-called package insert and are typically provided in paper media. The instructions are not so limited and may be provided in the form of electronic media (e.g., web sites, electronic mails, and the like provided on the Internet).

The amount of a composition and medicament used in the process of the present invention can be easily determined by those skilled in the art with reference to the purpose of use, a target disease (type, severity, and the like), the patient's age, weight, sex, and case history, the form or type of the cell physiologically active substance, and the like.

The frequency of the treatment method of the present invention applied to a subject (or patient) is also determined by those skilled in the art with respect to the purpose of use, target disease (type, severity, and, the like), the patient's age, weight, sex, and case history, the progression of therapy, and the like. Examples of the frequency include once per day to several months (e.g., once per week to once per month). Preferably, administration is performed once per week to month with reference to the progression.

A composition and medicament of the present invention comprises a material or medical ingredient to be introduced into hosts. Such a material or medical ingredient may be a biological macromolecule Preferably, such a biological macromolecule is selected from the group consisting of a nucleic acid, a polypeptide, a sugar, a lipid, and a complex molecule thereof. Preferably, such a medical ingredient may be a nucleic acid encoding a polypeptide which is expressed in the host into which the ingredient is introduced.

A composition and medicament of the present invention may comprise one or more additional medical ingredients. Such a medical ingredient may be contained in the pharmaceutical composition. Examples of such a medical ingredient include, but are not limited to, those described below:

central nerve system drugs (e.g., general anesthetics, sedative-hypnotics, anxiolytics, antiepileptics, anti-inflammatory agents, stimulants, antihypnotics, antiparkinson agents, antipsychotics, combination cold remedies, and the like);

peripheral nerve agents (e.g., local anesthetics, skeletal muscle relaxants, autonomic nerve agents, antispasmodic agents, and the like);

sensory organ drugs (e.g., ophthalmological agents, otorhinolaryngological agents, antidinics, and the like);

circulatory organ drugs (e.g., cardiotonics, antiarrhythmics, diuretics, antihypertensive agents, vasoconstrictors, vasodilators, antihyperlipemia agents, and the like);

respiratory organ drugs (e.g., respiratory stimulants, antitussives, expectorants, antitussive expectorants, bronchodilators, collutoriums, and the like);

digestive organ drugs (e.g., stegnotics, antiflatuents, peptic ulcer agents, stomachics, antacids, cathartics, enemas, cholagogues, and the like);

hormone agents (e.g., pituitary gland hormone agents, salivary gland hormone agents, thyroid gland hormone agents, accessory thyroid gland hormone agents, anabolic steroid agents, adrenal gland hormone agents, androgenic hormone agents, estrogen agents, progesterone agents, mixed hormone agents, and the like);

urogenital organ and anal drugs (e.g., urinary organ agents, genital organs agents, uterotonics, hemorrhoid agents, and the like);

dermatologic drugs (e.g., dermatologic disinfectants, wound protecting agents, pyogenic disease agents, analgesics, antipruritics, astringents, antiphlogistics, parasitic skin disease agents, emollients, hair agents, and the like);

dental and oral agents;

drugs for other organs;

vitamin agents (e.g., vitamin A agents, vitamin D agents, vitamin B agents, vitamin C agents, vitamin E agents, vitamin K agents, mixed vitamin agents, and the like);

nutritive agents (e.g., calcium agents, inorganic preparations, saccharide agents, protein amino acid preparations, organ preparations, infant preparations, and the like);

blood and body fluid drugs (e.g., blood substitute agents, styptics, anticoagulants, and the like);

dialysis drugs (e.g., kidney dialysis agents, peritoneal dialysis agents, and the like);

other metabolic drugs (e.g., organ disease agents, antidotes, antabuses, arthrifuges, enzyme preparations, diabetic agents, and others);

cell activating agents (e.g., chlorophyll preparations, pigment agents, and the like);

tumor agents (e.g., alkylation agents, antimetabolites, antineoplastic antibiotic preparations, antineoplastic plant extract preparations, and the like);

radiopharmaceuticals;

allergy drugs (e.g., antihistamic agents, irritation therapy agents, non-specific immunogen preparations, and other allergy drugs, crude drugs and drugs based on Chinese medicine, crude drugs, Chinese medicine preparations, and other preparations based on crude drug and Chinese medicine formulation);

antibiotic preparations (e.g., acting on gram-positive bacteria, gram-negative bacteria, gram-positive mycoplasmas, gram-negative mycoplasmas, gram-positive rickettsia gramnegative rickettsia, acid-fast bacteria, molds, and the like);

chemotherapeutic agents (e.g., sulfa drugs, antitubercular agents, synthetic antimicrobial agents, antiviral agents, and the like);

biological preparations (e.g., vaccines, toxoids, antitoxins, leptospire antisera, blood preparations, biological test preparations, and other biological preparations, and antiprotozoal drugs, anthelmintics, and the like).

As used herein, molecular biological techniques, biochemical techniques, and microbiological techniques well known in the art are optionally used. These methods are described in, for example, Ausubel. F. A., et al., editors (1988), "Current. Protocols in Molecular Biology", Wiley, New York, N.Y.; Sambrook J., et al. (1987), "Molecular Cloning: A Laboratory Manual", 2nd Ed., Cold Spring Harbor Laboratory Press, Cold Spring Harbor, N.Y.; Bessatsu Jikken Igaku, "Idenshi-Donyu & Hatsugen-Kaiseki-Jikkenho" [Experimantal Medicine, Special Issue, "Experimental Methods for Gene Introduction & Expression Analysis", Yodo-sha, 1997; and the like.

Viruses (e.g., HVJ) proliferated in fertilized chicken eggs by inoculating seed virus thereinto may be generally used. Alternatively, viruses proliferated in a persistent infection line of cultured cells or tissues of a monkey or human is used (culture medium supplemented with a hydrolytic enzyme, such as trypsin or the like). Alternatively, viruses proliferated in cultured cells which are infected with a cloned viral genome to elicit persistent infection may be used in the present invention. These mutant lines can also be used in the present invention. In addition, viruses (e.g., HVJ, etc.), which can be obtained by other methods, can also be used. Recombinant HVJ (Hasan M. K. et al., Journal of General Virology, 78, 2813 to 2830, 1997; or Yonemitsu Y. et al., Nature Biotechnology, 18, 970 to 973, 2000) can be used. Any HVJ may be used. The Z line (e.g., Accession No. ATCC VA 2388 or one commercially available from Charles River SPAFAS) or the Cantell line (e.g., Johnston M. D., J. Gen. Virol., 56, 175-184, 1981 or one commercially available from Charles River SPAFAS) are more desirable.

BEST MODE FOR CARRYING OUT THE INVENTION

In one aspect, the present invention provides a system for introducing a biomolecule into a cell. The present system comprises 1) a biomolecule; 2) a viral envelope; and 3) a glycosaminoglycan The present invention revealed the effects of a glycosaminoglycan (for example, heparin) to improve introduction of a biomolecule into a cell by the use of a viral envelope. Although not wishing to be bound by any theory, it is now believed that addition of a glycosaminoglycan attains the effect of changing or weakening the strength of a cell, thereby enhancing introduction of a biomolecule into a cell Accordingly, a glycosaminoglycan molecule used may be any glycosaminoglycan, and preferably a glycosaminoglycan having a glucosamine residue may be used, and more preferably a heparin may be used. Although not wishing to be bound by any theory, it is now believed that a glycosaminoglycan is preferable since it has a glucosamine as a residue, it has the effect of facilitating passage through blood-brainbarrier. Among heparins used, heparins having high molecular weight (for example, 10,000Da or greater, more preferably, 11,000Da or greater, still more preferably, 12,000Da or greater) are preferable, and more preferably, heparins having an average molecular weight of 12,000 to 15,000Da are used. However, heparins having less than those, molecular weight may be used. A degree of sulfation appears to have some effect on efficiency of delivery. Accordingly, heparins having a pharmaceutically acceptable degree of sulfation are preferable heparins for use. As described above, molecules other than heparins may be used. Such a molecule includes but is not limited to for example, hyaluronic acid, chondroitin sulfate, dermatan sulfate, keratan sulfate, heparan sulfate, and mixtures and polymers thereof. Although not wishing to be bound by any theory, it is believed that these molecules have sulfate residues, and thus facilitate delivery into the body. Such glycosaminoglycan is usually comprised in the system of the present invention at 1 U/ml. Preferably, such a glycosaminoglycan is comprised of at least 5 U/ml, more preferably of at least 10 U/ml, still more preferably of at least 50 U/ml, most preferably of at least 10.0 U/ml in the system of the present application.

In one embodiment, the viral envelope used in the present invention is inactivated. Such inactivation includes but is not limited to inactivation by ultraviolet ray radiation, alkylation and the like.

In one embodiment, the viral envelope used in the present invention may be an envelope of an RNA virus. Preferably, such a viral envelope may be an envelope of a virus belonging to the *Paramixovirus* genus (for example, HVJ, influenza virus), preferably, an HVJ envelope.

A biomolecule to be introduced by the system according to the present invention, may be any molecule as described hereinabove, and usually includes a molecule selected from the group consisting of a nucleic acid, polypeptide, lipid, sugar, and a complex molecule thereof. Preferably, such a biomolecule comprises a nucleic acid and polypeptide. In one embodiment, such a biomolecule comprises a nucleic acid. In another embodiment, such a biomolecule includes a polypeptide.

In a certain embodiment, a biomolecule to be introduced by the present invention is a nucleic acid encoding a gene selected from the group consisting of Vascular endothelial growth factor (VEGF), Fibroblast growth factor (FGF), and Hepatocyte growth factor (HGF).

In another embodiment, a molecule to be introduced by the present invention is a polypeptide selected from the group consisting of Vascular endothelial growth factor (VEGF), Fibroblast growth factor (FGF), and Hepatocyte growth factor (HGF).

In a preferred embodiment, the glycosaminoglycan (for example, heparin), the biomolecule and the viral envelope may be comprised in the same composition. In this case, homogeneity thereof in the composition is not problematic.

In another preferred embodiment, the glycosaminoglycan (for example, heparin), the biomolecule and the viral envelope may be comprised in different compositions. In this case, two compositions may be administered concurrently or separately. Preferably, the biomolecule is comprised in the viral envelope, since the biomolecule is therefore efficiently delivered.

In another aspect, the present invention provides a method for introducing a biomolecule into a cell, comprising the steps of: 1) administering to a cell a composition comprising a viral envelope and a biomolecule; and 2) administering a glycosaminoglycan to the cell. Preferable embodiments of biomolecules (for example, nucleic acids or polypeptides), viral envelopes (for example, HVJ envelopes), and glycosaminoglycan (for example, heparins) used in the present invention are described hereinabove.

In the present invention, the step of administering a glycosaminoglycan (for example, heparin) can be simultaneous to, prior to, or after the step of administering the composition comprising the viral envelope and the biomolecule. Preferably, the glycosaminoglycan is administered simultaneously or just before the administration of the composition. More preferably, the composition and the glycosaminoglycan are administered simultaneously. When the simultaneous administration is performed, glycosaminoglycans may or may not be contained in the composition.

In another aspect, the present invention provides for the use of glycosaminoglycan for manufacturing a medicament for introducing a biomolecule into a cell. In the present use, the claimed medicament comprises 1) a biomolecule; 2) a viral envelope; and 3) a glycosaminoglycan. Preferable embodiments of the biomolecule (for example, nucleic acid and polypeptide), a viral envelope (for example, HVJ envelope) and a glycosaminoglycan (for example, heparin) are described hereinabove.

In another aspect, the present invention provides a method for delivering a biomolecule to a brain. This method comprises the steps of: 1) transiently occluding an artery of the head portion or cervical portion; and 2) introducing a biomolecule into the brain during the occluding of the artery of the head portion or the cervical portion. As used herein, it was an unexpected effect that the biomolecules can be introduced with high efficiency (for example, two fold or greater) to the brain by transiently occluding an artery, since it was thought that the biomolecules cannot be introduced to the brain by the clear distinction of the blood vessel and the brain, due to the presence of the blood-brain-barrier (BBB). Methods for transient occlusion include balloon cathethers, clipping, cerebral infarction as a physiological occlusion, and the like. Preferably, balloon cathether and clipping are used. As used herein, "transient" refers to a period of time sufficient for administering a biomolecule (for example, at least one minute, 5 minutes and the like), and preferably 1-120 minutes.

In one embodiment, a biomolecule may be any molecule as described herein above, and preferably is selected from the group consisting of a nucleic acid, a polypeptide, a lipid, sugar, and a complex molecule thereof. In a preferable embodiment, the biomolecule comprises a nucleic acid.

In a preferable embodiment, the biomolecule is a nucleic acid molecule encoding a gene selected from the group consisting of vascularization factors such as vascular endhothelial growth factor (VEGF), fibroblast growth factor (FGF), hepatocyte growth factor (HGF), HIF-1, DEL-1 and the like; an antiapoptosis agent such as Bcl-2 and the like; a brain protective agent such as BDNF and the like; or antioxidant agents such as Mn—SOD and the like.

In a preferable embodiment, the nucleic acid to be introduced is delivered by a vector. Such a vector optionally includes a transcription regulation sequence such as a promoter, an enhancer, and the like. Preferably, a vector may be an expression vector. Construction of a vector is well known in the art.

In one embodiment, a biomolecule is introduced with an vital envelope. Preferably, the viral envelope to be used in the present invention is inactivated. Inactivation reduces unwanted toxicity or the like. Inactivation may be achieved by any method including but not limited to, UV radiation, use of alkylating agent and the like.

In another embodiment, the viral envelope may be an envelope of an RNA virus. Preferably, the viral envelope used is an envelope of a virus belonging to the *Paramixovirus* genus (for example, HVJ, influenza virus). Most preferably, the viral envelope used is an envelope of an HVJ.

In a preferable embodiment, introduction to a brain of a biomolecule may be performed together with a glycosaminoglycan. Glycosaminoglycan may be any molecule, and preferably, a heparin. Any glycosaminoglycan may be used, and preferably the molecular weight of the glycosaminoglycan is at least 10,000 Da, more preferably, at least 11,000 Da, more preferably, at least 12,000 Da. In a preferable embodiment, the molecular weight of a heparin is 12,000 to 15,000 Da.

In one embodiment, glycosaminoglycan used is comprised of at least at 50 U/ml.

As used herein, it is preferable that the degree of sulfation of the glycosaminoglycan (for example, heparin) is pharmaceutically acceptable.

In one embodiment, the glycosaminoglycan may be administered simultaneously with, prior to, or after the administration of the biomolecule. Preferably, the glycosaminoglycan and the biomolecule are administered simultaneously.

In a preferable embodiment, the artery of the head portion or cervix portion is occluded for 1 to 120 minutes.

In one embodiment, the artery of the head portion or the cervical portion is the middle cerebral artery or the carotid artery. In a preferable embodiment, the artery of the head portion or the cervical portion is the middle cerebral artery.

In one embodiment, the biomolecule is administered into the carotid artery or the thalamus, intracerebroventricularly or intrathecally.

In a preferable embodiment, the biomolecule is administered into the carotid artery. The carotid artery is preferable since it supplies blood to a wide range of the brain parenchyma.

In another aspect, the present invention provides a kit for delivering a biomolecule to a brain. The kit comprises 1) a biomolecule; and 2) an instruction indicating a method for administering the biomolecule the method comprising: A) transiently occluding an artery of a head portion or a cervical portion; and B) introducing the biomolecule into the brain during the occluding of the artery of the head portion or the cervical portion. A method for transient closure is described hereinabove.

The biomolecule to be included in a kit may be any molecule but preferably is selected from the group consisting of a nucleic acid, a polypeptide, a lipid, a sugar, and a complex molecule thereof. Preferably, the biomolecule comprises a nucleic acid.

As used herein preferable biomolecules are a nucleic acid molecule encoding a gene selected from the group consisting of vascularization factors such as vascular endhothelial growth factor (VEGF), fibroblast growth factor (FGF), hepatocyte growth factor (HGF), HIF-1, DEL-1 and the like; an antiapoptosis agent such as Bcl-2 and the like; a brain protective agent such as BDNF and the like; an antioxidant agent such as Mn—SOD and the like.

The nucleic acid included in the kit is delivered by a vector. Vectors as used herein may be any one as long as the vector can express such a nucleic acid. Preferably, a vector is used which can efficiently express the nucleic acid in a mammal (preferably human).

In a preferable embodiment, the kit of the present invention further comprises a viral envelope.

The viral envelope is preferably inactivated so adverse effects may be avoided.

Preferably, the viral envelope may be an envelope of an RNA virus.

More preferably, the viral envelope is an envelope of a virus belonging to the *Paramixovirus* genus (for example, HVJ, influenza virus, and the like).

Most preferably, the viral envelope is an HVG envelope.

The kit of the present invention may further comprise a glycosaminoglycan.

As used herein, the glycosaminoglycan used is preferable, but not limited to, heparin In one embodiment, the molecular weight of the glycosaminoglycan used is at least 10,000 Da, more preferably at least 11,000 Da, more preferably at least 12,000 Da. More preferably, the molecular weight of heparin is 12,000-15,000 Da.

In one embodiment, the glycosaminoglycan, to be included in the kit of the present invention is comprised at least at 50 U/ml.

In a preferable embodiment, the degree of sulfation of the glycosaminoglycan (for example, heparin) is pharmaceutically acceptable.

In a preferable embodiment, the glycosaminoglycan is administered simultaneously with, prior to, or after the administration of the biomolecule. More preferably, the biomolecule and the glycosaminoglycan are administered simultaneously.

In a preferable embodiment of the kit of the present invention, the artery of the head portion or the cervical portion is occluded for 1 minute to 120 minutes. In a preferable embodiment, the artery of the head portion or the cervical portion is the middle cerebral artery or the carotid artery. Further, the artery of the head portion or the cervical portion is the middle cerebral artery.

In a preferable embodiment of the kit of the present invention, the biomolecule is administered into the carotid artery or the thalamus, intracerebroventricularly or intrathecally, but the present invention is not limited thereto.

In a preferable embodiment of the kit of the present invention, the biomolecule is administered; into the carotid artery.

In another aspect, the present invention provides for the use of a biomolecule for manufacturing a kit for delivering a biomolecule into the brain. The kit comprises A) the biomolecule; and B) an instructions for indicating a method for administering the biomolecule the method comprising: a) transiently occluding an artery of a head portion or a cervical portion; and b) introducing the biomolecule into the brain during the occluding of the artery of the head portion or the cervical portion.

As such, the present inventors have studied the possibility of gene delivery into the CNS using a viral envelope (for example, HVJ-E vector) both in vitro and in vivo, in the present invention. As demonstrated by the following Examples, when using a Venue reporter gene, fluorescence was able to be detected in a rat cerebral cortex neuron and a glial cell. By direct injection into the thalamus, intracerebdovetricularly, or intrathecally, reporter genes (Venus or EGFP) were successfully transfected into rat brain without induction of immunological response. Gene expression was not observed after the intraartery injection via total cervical artery, however, when a vector was injected into the middle cerebral artery after transient closure, EGFP or luciferase activity was only detectable in the damaged hemisphere. Lastly, in order to increase the transfectino efficiency, the effect of heparin was examined. Luciferase activity was significantly increased by the addition of 50 U/ml heparin ($p<0.05$).

In conclusion, the HVJ-E vector is highly efficient for transfection of a gene into the CNS with out any evident toxicity. HVJ-E vector is useful for examining the role of a number of genes and for treating cerebrovascular diseases.

Hereinafter, the present invention is described based on the Examples. The following examples are provided only for exemplary purposes. Accordingly, the scope of the present invention is not limited to the above description and the following examples, and merely limited by the appended claims.

EXAMPLES

Example 1

A method using HVJ

Materials and Methods

HVJ-Envelope Vector

Induction HVJ (Z strain) (10,000 hemagglutinating units) was mixed with plasmid DNA (200 µg) and 0.3% Triton-X. The mixture was washed with balanced salt solution (BSS; 137 mM NaCl; 5.4 mM KCl and 10 mM Tris-HCl, pH 7.6). It was then suspended in 10 μl (for intracerebral administration), 100 μl (for intrathecal or intraartery administration), or 400 μl (for culturing cells) phosphate-buffered saline (PBS; pH 7.5). For in vitro studies, protamine sulfate (Nakalai, tesque, Japan) was added to the culture plate 10 μg/well) before treatment with the vector to enhance the transfection efficiency. In the case of co-injection with heparin (Aventist Japan), low molecular weight heparin (Fragmin®, Kissei, Japan), or argatroban (Slonnon®, Daiichi, Japan), they were mixed with PBS and added to the vector.

Plasmid DNA pEGFP-C1 was purchased from Clontech (CA, USA). pCMV-luciferase-GL3 (pcLuc-GL3-7.4 kb) was constructed by cloning the luciferase gene from the pGL3-Promoter Vector (Promega, Madison, Wis., USA) into pcDNA3 (5.4 kb) (Invitrogen, San Diego, Calif., USA) at the HindIII and BamHI sites. Plasmids were purified with the Qiagen plasmid isolation kit (Hilden, Germany). pCMV-LacZ (9.2 kb) was constructed by inserting the Hind III-Bam HI fragment of pSV-β-galactosidase (Promega) into pcDNA3.

Venus/pCS2 was kindly provided by Dr. Nagai (Laboratory for Cell Function and Dynamics, Advanced Technology Development Center, Brain Science Institute, RIKEN, Japan).

(Determination of Fluorescence Due to Venus)

Expression of Venus was examined under a fluorescent stereomicroscope 96 hours after injection. More precise images were obtained with a confocal laser microscope (Bio-Rad, Hercules, Calif., USA).

(Assay for Luciferase Activity)

Rats transfected with the luciferase gene were sacrificed under anesthesia at 24 hours after transfection. Organ (brain, lung, spleen and liver) were harvested and placed individually in FALCON 50 ml tubes. The luciferase activity assay was performed as described previously [Brewer G J, Torricelli J R, Evege E K, Price P J., J Neurosci Res. 1993; 35:567-76.]. Luciferase levels were normalized by determining the protein concentrations of the tissue extracts [Brewer G J, Torricelli J R, Evege E K, Price P J., J Neurosci Res. 1993; 35:567-76.]. Luciferase units were expressed as relative light units (RLU) per gram of tissue protein.

(In vitro Gene Transfer)

Rat embryonic cerebral cortex neurons were obtained from pregnant Wistar rats at 19 days gestation (Charles River Japan, Atsugi, Japan) and cultured [Be-layev L, et al., Stroke. 1996; 27:1616-22; discussion 1623FF09]. Briefly, the cerebral cortex was dissected and individual cells were isolated by treatment with papain and triturated in Leibovitz s L-15 medium (Invitrogen, CA, USA). Cells were cultured in poly-D-lysine-coated 24-well plastic culture dishes with DMEM (Invitrogen)/B-27 (Invitrogen) at 37° C. in a humidified atmosphere of 95% air-5% $CO_2$. The medium was changed on the first and fourth days. The rate of immuno-positive cells for $MAP_2$ (microtubule-associated protein) on the seventh day was 92.9%. Before transfection, the medium was changed to fresh 500 μl DMEM/well. HVJ-E vector (250 HAU) containing the Venus gene was added to each well and left for 10 min at 37° C. After transfection, the medium was changed to fresh DMEM/B-27 and the dishes were incubated at 37° C. The expression of Venus was observed at 2 days after transfection using laser scanning confocal microscopic images. Transfection efficiency (%) was calculated as (the number of cells expressing Venus/the number of NeuN immunoreactive cells)×100. To average the efficiency, five visual fields were randomly selected and the number of cells was counted.

(Immunohistochemistry)

In vitro cultured cells were fixed with 4% paraformaldehyde at 37° C. for 15 min and treated with 0.5%, Triton X-100 for 10 min. The cells were blocked with PBS containing 2% goat serum, bovine serum albumin (5 mg/ml), and glycine (50 mM). Then, the cells were incubated with a mouse monoclonal antibody against $MAP_2$ (1:1000, Sigma-Aldrich, Saint Louis, Mo., USA) or a mouse monoclonal antibody against GFAP (Glial Fibrillary Acidic Protein, 1:1000, Sigma-Aldrich) overnight at 4° C. After washing with PBS, Alexa Fluor 546-conjugated goat anti-mouse IgG (Molecular Probes, Eugene, Oreg., USA) was applied as a secondary antibody and the dishes were incubated for 1 hour at room temperature. The image was analyzed with a confocal laser microscope.

(In Vivo Gene Transfer in Normal Rats)

Wistar male rats (270-300 g; Charles River Japan, Atsugi, Japan) were used in the present invention. All procedures were conducted in accordance with Osaka University guideline. Rats were anesthetized with ketamine (Sankyo, Japan) and placed in a stereotactic frame (Narishige Scientific Instrument Laboratory, Tokyo, Japan), with the skull exposed. A stainless steel canula (30 gauge; Becton-Dickinson, Franklin Lakes, N.J.) with a specially designed Teflon connector (FEP tube, Bioanalytical systems, West Lafayette, Ind.) was introduced into the thalamus (3.8 mm posterior to the bregma, 2.4 mm lateral to the midline, and 5.0 mm below the skull surface) or lateral ventricle (0.48 mm anterior to the bregma, 0.8 mm lateral to the midline, and 3.8 mm below the skull surface). The HVJ-E vector containing the Venus gene or EGFP gene was injected at a speed of 1.0 μl/min. After infusion, the infusion cannula was removed. No behavioral change such as convulsion or abnormal movement of extremities was observed in any animal.

For infusion into the subarachnoid space, the head of each animal was fixed in the prone position and the atlanto-occipital membrane was exposed through an occipitocerebral midline-incision. A stainless steel cannula (27 gauge; Becton-Dickinson) was introduced into cisterna magna (subarachnoid space). HVJ-E vector (100 μl) containing luciferase or Venus gene was infused at a speed of 50 μl/min after removing 100 μl CSF. Then, the animals were placed head down for 30 min. For infusion into the common carotid artery, the left common carotid artery, the left external carotid artery, and the left internal carotid artery were isolated via a midline incision under an operating microscope (Konan, Japan). The left common carotid artery and internal carotid artery were ligated temporally and a PE-50 catheter (Clay Adams, Parsippany, N.Y., USA) was introduced into the left common carotid artery via a cutdown in the left external carotid artery. HVJ-E vector (100 μl) containing EGFP or luciferase gene was injected at a speed of 25 μl/min. After injection, the cannula was removed and blood flow to the common carotid artery was restored by release of the ligatures. In each procedure, EGFP or Venus was observed at 4 days after transfection and luciferase activity was measured at 1 day after transfection. Luciferase activity in spleen, lung, and liver was also measured at 1 day after intrathecal injection. All rats showed no weight loss or loss of, activity after administration. To clarify the histological change after administration of vector, HE staining of coronal section was performed at 14 days after intraventricle and intrathecal injections. The coronal sections were made at +1.0 mm, −3.30 mm, −5.30 mm, −11.30 mm, and −14.60 mm from the bregma.

(In vivo Gene Transfer after Transient Middle Cerebral Artery Occlusion)

To make the middle cerebral artery occlusion model, the left middle cerebral artery was occluded by placement of poly-L-lysine coated 4-0 nylon at the origin of MCA as described before [Belayev L et al., Stroke 27, 1616-1622 (1996)]. Briefly, animals were anesthetized with halothane (1-3.5% in a mixture of 70% $N_2O$ and 30% $O_2$) using a face mask. The rectal temperature was maintained at 37±1° C. throughout the surgical procedure using a feedback regulated heating pad. Under the operating microscope the left common carotid artery, the left external carotid artery, and the left internal carotid artery were isolated via a midline incision. After 60 min, common carotid artery and internal carotid artery were transiently ligated and the 4-0 nylon was removed and reperfused for 10 minutes. The common carotid artery and the internal carotid artery were then transiently ligated again. The PE-50 catheter was placed at the common carotid artery from external carotid artery as described above, and the vector was injected at the speed of 10 µl/min after the release of ligation. After injection, the PE-50 catheter was removed and the external carotid artery was ligated by 6-0 nylon. The expression of luciferase or EGFP was observed at 1 day or at 3 days after the infusion.

Results (Transfection into the Cultured Rat Cerebral Cortex Cells)

In order to develop an effective method for transferring a gene into the CNS, we transfected the reporter gene (Venus gene) into cultured rat cerebral cortex cells (E19), since Venus reporter gene has been reported as an easily detected transfection method. It is reported that the use of Venus as an acceptor allows reliable early detection of fluorescence signals in brain slices [Nagai T, et al., Nat Biotechnol. 2002; 20:87-90.]. At 2 days after transfection, the cultured rat cerebral cortex cells demonstrated readily detectable fluorescence in cultured cells (FIGS. 1a, 1d and 1g). Using immunohistochemical staining, the cells were immuno-positive for $MAP_2$ (microtubulue associated protein 2; the neuronal marker), NeuN (neuron nuclear antigen: the neuron marker) or GFAP (glial fibril acidic protein; the glial and astrocytic marker) (FIGS. 1c, 1f and 1i). The efficiency of transfection into neuronal cells as calculated from the number of Venus positive cells/the number of NeuN positive cells was 26.7±6.4%, while no positive cells could be detected in cells transfected with a control vector. No cell death was not observed after transfection using HVJ-E vector.

(In vivo Gene Transfer into the Brain)

Figure 2:
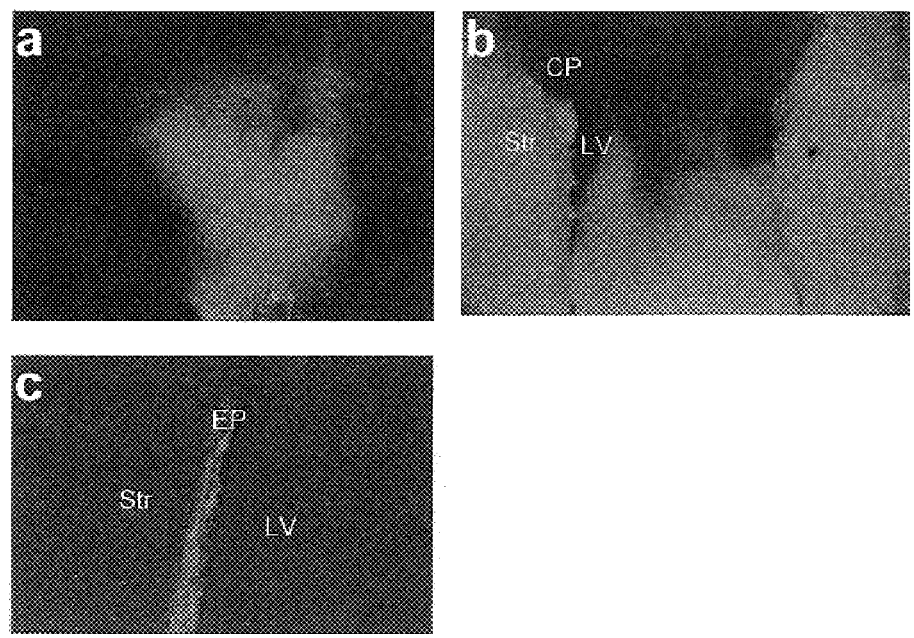
FIG. 2. In vivo gene transfer of a EGFP plasmid into brain using stereotactic injection. A fluorescent stereomicroscope image of laser scanning confocal microscopy images. Stereotactic injection into the thalamus showed limited expression at the site of injection (a). Stereotactic injection into the lateral ventricle revealed expression at the choroid plexus (b) and ependymal cells (c). CP, choroid plexus; LV, lateral ventricle; Str, striatum; Ep, ependymal cell layer. This experiment was repeated at least three times.
Figure 3:
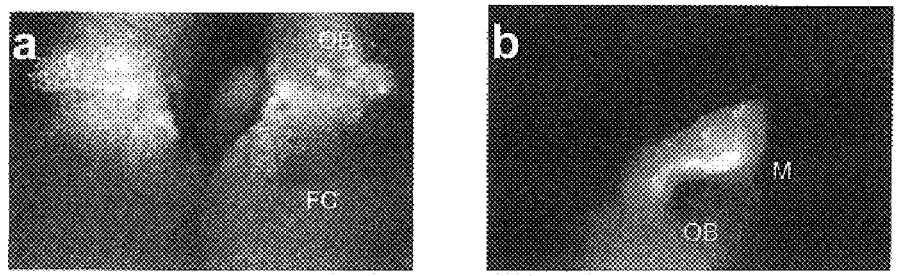
FIG. 3. In vivo gene transfer of Venus plasmid into brain by the injection via cisterna magna. OB: olfactory bulb; FC: frontal cortex, M: meninges. This experiment was repeated at least three times.

Then, we examined the transfection of Venus gene into the brain. Initially, we injected the HVJ-E vector containing enhanced green fluorescence protein (EGFP) gene into the thalamus and lateral ventricle. Stereotactic injection of EGFP gene into the thalamus showed the limited expression at the site of injection (FIG. 2a). Fluorescence could be detected at the choroids plexus and ependymal cells (FIGS. 2b and 2c) after stereotactic injection into the lateral ventricle. Unexpectedly, no fluorescent signal was detected in neurons. On the other hand, no positive staining for fluorescence could be detected in the brain transfected with the control vector or in the untransfected brain. Then, we did injections into the subarachnoid space. In this experiment, we used the Venus reporter gene instead of EGFP, since the use of the Venus reporter gene is an easily detectable transfection method. Injection into cerebral spinal fluid via cisterna magna caused widespread Venus expression in meningis, but less expression in chorioid plexus or neuron (FIGS. 3a and 3b). Importantly, HE staining of coronal section at 3 days after intrathecal injection showed no inflammatory change.

(Gene Transfer into CNS after Transient Middle Cerebral Artery Occlusion)

Figure 4:
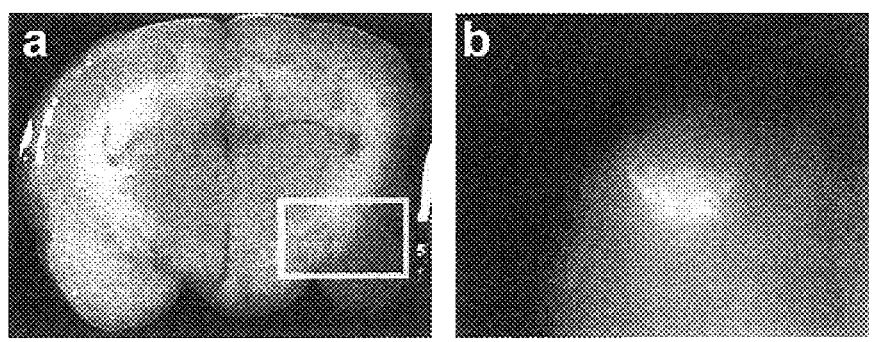
FIG. 4. Fluorescence due to Venus gene transfer via carotid artery after transient occlusion of middle cerebral artery. Coronal suture section at 3 days after left transient occlusion of middle cerebral artery for 60 minutes and a fluorescent stereomicroscope image. HVJ-E vector having. Venus gene was infused in the left carotid artery during the reperfusion. Gene expression was observed only at the injured lesion, while no fluorescence could be detected at the intact hemisphere. This experiment was repeated at least three times.
Figure 5:
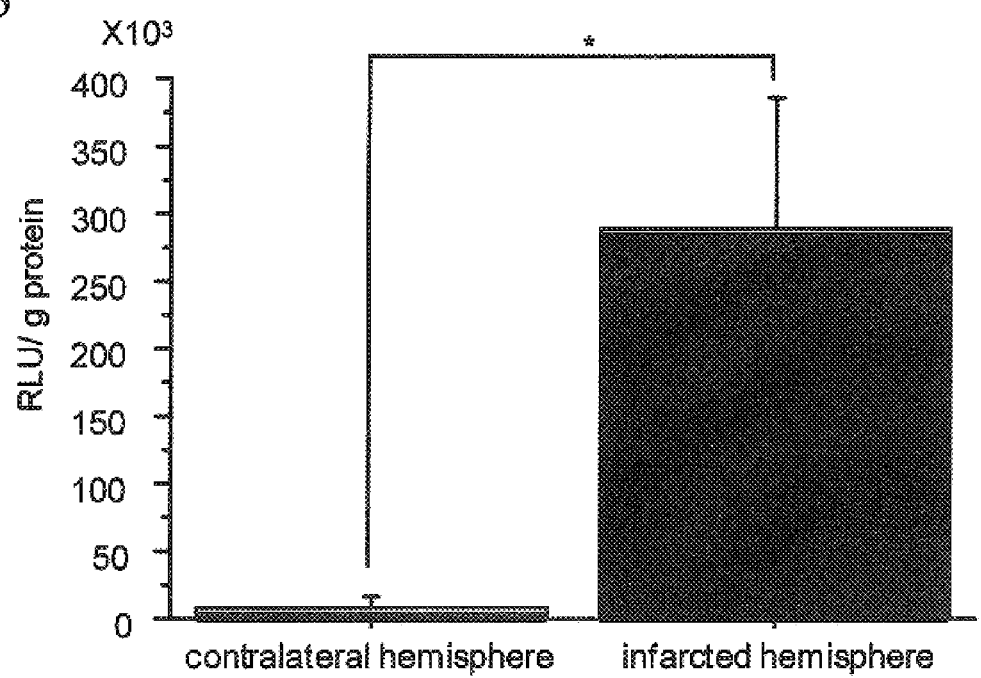
FIG. 5. Luciferase activity in injured hemisphere and the contra lateral hemisphere after gene transfer into carotid artery after transient occlusion of middle cerebral artery. Luciferase activity was measured at day 1 after left transient occlusion of middle cerebral artery for 60 minutes. HVJ-E vector containing luciferase gene was infused in the left carotid artery during the reperfusion. n=5 for each group.

Considering the treatment of cerebral ischemic disease in the clinical setting, it seems best to employ infusion into the subarachnoid space rather than injection into the lateral ventricle using a stereotactic frame. To further explore the feasibility of gene therapy using HVJ-E vector in cerebral ischemia, we examined gene transfer into CNS via the carotid artery. However, intraarterial infusion into the carotid artery produced little expression of the transgene in the brain and microvascular endothelial cells at 3 and 7 days after injection. To overcome this issue, we hypothesized that gene transfer after brain ischemia might show different transfection efficiencies into CNS, since brain ischemia caused a change in the blood-brain barrier [Belayev L, Busto R, Zhao W, Ginsberg M D., Brain Res. 1996; 739:88-96.; Kuroiwa T, Ting P, Martinez H, Klatzo I., Acta Neuropathol. 1985; 68:122-9.; and Neuann-Haefelin T, et al., Stroke. 2000; 31:1965-72; discussion 1972-3.]. Thus, we infused HVJ-E vector including the Venus gene into the carotid artery after transient middle cerebral cerebral artery occlusion for 60 min. Interestingly, fluorescence due to Venus could be detected at the infarcted cerebral cortex at 3 days after transient occlusion (FIG. 4). The feasibility of transfection into CNS was confirmed by experiments using the luciferase. gene. Luciferase activity at 24 hours after injection was much higher in infarcted hemisphere than that in contra lateral hemisphere (FIG. 5, $P<0:05$). On the other hand no luciferase activity was detected in the spleen, lung and liver.

Figure 6:
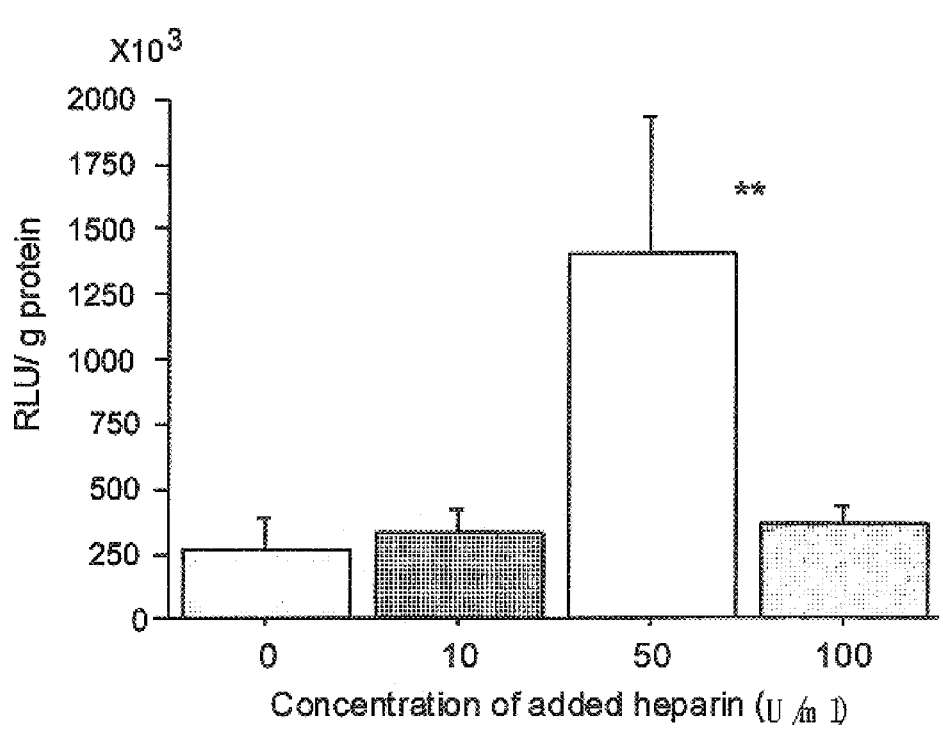
FIG. 6. Effect of heparin on luciferase activity. Luciferase activity was measured at day 1 after transfection of pGL3 luciferase gene via cisterna magna. Heparin was added to the vector at the concentration of 0, 10, 50, or 100 (U/ml), low molecular weight heparin at 10, 50, or 100 (U/ml). **$P<0:01$ vs. 0, 10 and 100. n=3 for each group.

Finally, we investigated whether co-administration of heparin would increase the transfection efficiency. After the making of HVJ-E vector containing luciferase gene, heparin was added into the vector at concentrations of 10, 50 or 100 U/ml. The HVJ-E vector was injected into CSF via the cisterna magna. As shown in FIG. 6, luciferase activity was dramatically enhanced on the addition of 50 U/ml heparin ($P<0:05$). To clarify the mechanism of the increase In transfection efficiency with heparin, we examined the effects of low molecular weight heparin (LMWH) at the concentrations of 1, 5, 10, 50, 100 or 200 U/ml, or argatroban at a concentration of 0.1 or 0.2 mg/ml. However, neither low molecular weight heparin nor argatroban affected the luciferase activity.

(Discussion)

Previously, we have reported the efficacy of an HVJ-liposome transfection method for the CNS in rats and in primates [Yamada K, et al., Am J Physiol. 1996; 271:R1212-20.; Hagihara Y, et al., Gene. Ther. 2000; 7:759-63.; and Hayashi K, et al., Gene Ther. 2001; 8:1167-73.]. The HVJ-liposome method utilized the combination of liposomes and fusion activities of proteins derived from the HVJ envelope [Kaneda Y, Saeki Y, Morishita R., Mol Med Today. 1999; 5:298-303.] for various cells and tissues. However, the procedure to make HVJ-liposome vesicleis time-consuming and complex. In addition, long-term storage be impossible. These issues might affect the usage of HVJ-liposome complex for human gene therapy. To overcome these problems, we have recently developed the second generation of HVJ vector, so-called HVJ-envelope (HVJ-E) vector. In order to produce HVJ-E vector, a transgene was inserted into the envelope of HVJ after the viral genome thereof had been completely disrupted. The advantages of HVJ-E vector as compared to those of HVJ-liposome vector are: (1) it is easy to make, (2) the production does not take much time (less than 90 min), and (3) that HVJ-E can be stored for a long period time (at least six months). In the present invention, we have demonstrated the possibility of gene transfer into the ONS using the HVJ-E vector both in vivo and in vitro. In the in vitro study, reporter genes were successfully expressed in neuron (MAP$_2$ positive cells or NeuN positive cells) and astroglial cells (GEAP positive cells) without inducing cell death. With non-viral vector, mitotic cells are transfected well, but non-mitotic cells such as quiescent (G$_o$) neurons are transfected poorly [Berry M, et al., Curr Opin Mol Ther. 2001; 3:338-49.]. However, in the present invention, reporter. genes were successfully transfected into non-mitotic cells with the HVJ-E vector Effective transfection can be attained due to the presence of a virus reporter against sialic acid, which is enriched on the surface of a neuron.

Importantly, the distribution of gene expression with HVJ-E vector was different from that with HVJ-liposome for in vivo gene transfer. By intrathecal injection, β-galactosidase gene expression was observed in cerebral parenchyma by HVJ-liposome method [Hagihara. Y, et al., Gene Ther. 2000; 7: 759-63.; and Hayashi K, et al., Gene Ther. 2001; 8: 1167-73.], while gene expression was detected only in the meningotheles and adventitial cells of artery using HVJ-E vector. Additionally, intraventicle cationic-liposome-mediated (HVJ cationic liposome mediated) gene transfer showed expression in cerebral parenchyma [Zou L L, et al., Gene Ther. 1999; 6: 994-1005.], whereas HVJ-E vector-mediated gene transfection revealed transgene expression only at the choroid plexus and ependymal cells. Considering the fact that the direct injection of HVJ-E vector into thalamus resulted in successful transfection into cerebral parenchyma, the presence of liposome might be important to cross over the meninx or ependymal cells. The present inventors and others have reported some gene transfer methods of high transfection efficiency for use in lateral ventricle administration using a stereotactic frame (Yoshimura S. et al., Hypertension. 2002; 39:1028-34.; and Yukawa H. et al., Gene Ther. 2000; 7:942-9.), however, such technology is quite invasive. Luckily, the present inventors have found that transgene expression was observed on the brain surface after infusion into the cisterna magna. Further, the present invention clearly demonstrates that gene transfer into the CNS is possible after transient middle cerebral artery via intraartery injection of the HVJ-E vector upon re-opening the artery. The destruction of the blood-brain barrier occlusion is controversial [Belayev L, Busto R, Zhao W. Ginsberg M D., Brain Res. 1996; 739:88-96.; Kuroiwa T, Ting P, Martinez H, Klatzo I., Acta Neuropathol. 1985; 68:122-9.; and Neumann-Haefelin T, et al., Stroke. 2000; 3 1:1965-72; discussion 1972-3.]. Kuroiwa et al. demonstrated a biphasic opening of the blood brain barrier after 1 hour of transient middle cerebral artery occlusion, occurring first at 15 mm after the release of occlusion, then at 5 and 72 h of reperfusion (Kuroiwa T, Ting P, Martinez H. Klatzo I., Acta Neuropathol. 1985; 68: 122-9.). Infusion of HVJ-E vector during this limited time period would allow us to transfect therapeutic genes into cerebral parenchyma via intraarterial means. It should be noted that coadministration of heparin increased efficacy of transfection with HVJ-E vector. This result is similar to the report in which co-infusion with heparin using AAV vector induced higher and more homogeneous gene expression [Mastakov MY, Baer K, Kotin R M, During M J., Mol Ther. 2002; 5:371-80. 29.; and Nguyen J B, Sanchez-Pernaute R, Cunningham J, Bankiewicz K S., Neuroreport. 2001; 12:1961-4.]. It was predicted that heparin affects 2,3-linked sialic Teoglyacid;, a virus binding receptor, to enhance efficiency of transfection, or heparin binds to the viral surface to limit interaction with HSPG on the cellular surface. To clarify the mechanism we examined the effects of low molecular weight heparin (LMWH) and similar substances such as argatroban. However, no increase in transfection efficiency was observed using these molecules. The difference between conventional heparin (12,000-15,000 Da) and LMWH (5000 Da) is only the molecular size and the degree of sulfation [Ishai-Michaeli R. et al., Biochemistry. 1992; 31:2086-B.]. These factors likely influence the interaction between HVJ-E vector and targeted cell surface.

Here, the present invention demonstrated potent transfection efficiency using HVJ-E vector into the CNS in vivo as well as In vitro without any apparent toxicity, while the site of gene expression was different among various administration routes. Successful gene transfection by intra-arterial injection after transient arterial occlusion provides a promising approach for treatment of cerebral ischemia. In addition, to our knowledge, there has been no evidence of side effects. HVJ is not pathogenic to humans [Okada Y., Methods Enzymol 1993; 2211, 18-41.; and Okada Y, Tadokoro J., Exp cell Res 1962; 26,108-118.] and is completely inactivated by appropriate chemical modification without losing fusion activity. In the present invention, intrathecal or intraventricular administration showed no loss of weight, no neurological deficits, and no inflammatory change. Additionally, no luciferase activity was observed at any other organs after intrathecal injection. Therefore, the HVJ-E vector seems to be safe for transfection into the brain. With respect to immunogenicity, five rounds of repeated administrations of plasmid DNA and antisense decoy DNA oligonucleotide (ODN) by HVJ-liposome method did not result in any loss of biological effects or production of antibodies against HVJ (Morishita R, Gibbons G H, Kaneda Y. Ogihara T. Dzau V J., Biochem Biophys Res Commun 2000; 273: 666-674; and Hirano T, et al., Gene Ther 1998; 5: 459-464.). For these reasons, HVJ-E vector may be a suitable gene transfer method for the treatment of cerebrovascular disease.

Example 2

Delivery Using Other Vital Vectors (Preparation of Influenza Virus)

Influenza virus belonging to the Orthomixovirus family was obtained from fertilized chicken egg and propagated basically in accordance with WO96/05294. Briefly, it was performed as follows: fertilized eggs need to be carefully selected and obtained from specially secured healthy farms. The eggs are placed in an incubator at 37.8° C. (100° F.) for from 9 days to 12 days. The egg is held to the light of a candle to observe the growth or survival of the embryo before an influenza virus is inoculated into the allantois.

Thereafter, in order to infect the egg with the virus under optimal conditions, the egg is cultured for from 2 days to 3 days in a culture incubator having controlled temperature and humidity. The conditions vary depending on the line and type of the influenza virus used. The culture is rapidly cooled to 5±3° C. to arrest the proliferation of the virus. Thereafter, allantois liquid containing a large amount of virus particles is recovered from the infected egg. The thus-obtained allantois liquid containing the influenza virus needs to be rapidly purified to remove impurities, such as proteins (e.g., ovalbumin, etc.), lecithin, bacteria, and the like. To achieve this, the recovered material is centrifuged to remove the supernatant, followed by ultrafiltration to condense the material 20-fold before purification of the virus.

(Alkylation Process)

Immediately before use, 0.01% β-propiolactone was prepared in 10 mM KH$_2$PO. This procedure was rapidly performed at low temperature.

β-propiolactone was added to the influenza virus condensate solution obtained as mentioned above, followed by incubation on ice for 60 minutes. Thereafter, incubation was performed at 37° C. for 2 hours. The resultant solution was dispensed into Eppendorf tubes, followed by centrifugation at 15,000 rpm for 15 minutes. The precipitate was preserved at −20° C. Optionally, this influenza virus was ultrafiltered.

Ultrafiltration using 500 KMWCO (A/G Technology, Needham, Mass.) was used to condense the chorioallantoic fluid about 10-fold. 50 mM NaCl, 1 mM $MgCl_2$, 2% mannitol, 20 mM Tris (pH 7.5) was used as buffered solution. The HA assay was used to achieve an influenza virus envelope recovery rate of substantially 100%. This is an excellent result.

Column chromatography was performed using Q-SepharoseFF (Amersham Pharmacia Biotech K.K., Tokyo) (buffered solution: 20 mM Tris-HCl (pH 7.5) buffer, from 0.2 M to 1 M NaCl)) to purify influenza virus envelope. As a result, the recovery rate was from 40% to 50%, and the purity was 99% or more.

As such, inactivated influenza virus envelope was prepared from influenza virus containing chorioallantois liquid.

Delivery into the brain using the influenza viral envelope was investigated. We have investigated the possibility of gene transfer into the CNS using influenza virus envelope in vitro and in vivo as in Example 1. When using the Venus reporter gene, fluorescence could be detected in rat cerebral cortex neuron and glial cells. In in vivo experiment, reporter genes (Venus or EGFP) were successfully transfected into rat brain by direct injection into the thalamus, intracerebroventricular injection, or intrathecal injection without inducing immunological change. Gene expression was not observed after intraartery injection via common carotid artery, however, when the vector was injected into the middle cerebral artery after transient occlusion, EGFP or luciferase activities were only detected in the damaged hemisphere, Lastly, the effect of heparin on the increase of transfection efficiency was examined. Luciferase activity was significantly increased by the addition of 50 U/ml.

As such, it was demonstrated that not only HVJ-E vector, but also vectors derived from HVJ-E vectors significantly increased gene delivery efficiency into the brain after transient occlusion of cerebral artery, and the addition of heparin increased efficiency of biomolecule delivery with influenza virus envelope.

Example 3

A Method Using Adeno-Associated Virus

Next, adeno-associated virus was used to perform experiments similar to those of Examples 1 and 2. AAV Helper-Free System (Stratagene) was used as an adeno-associated virus.

The Alkylation process was performed as described in Example 2.

Delivery into the brain using an adeno-associated virus envelope was investigated. We have investigated the possibility of gene transfer into the CNS using adeno-associated virus envelope in vitro and in vivo as in Example 1. When using the Venus reporter gene, fluorescence could be detected in rat cerebral cortex neuron and glial cells, In in vivo experiment reporter genes (Venus or EGFP) were successfully transfected into rat brain by direct injection into the thalamus, intracerebroventricular injection, or intrathecal injection, without inducing immunological change. Gene expression was not observed after intraartery injection via common carotid artery, however, when the vector was injected into the middle cerebral artery after transient occlusion, EGFP or luciferase activities were only detected in the damaged hemisphere. Lastly, the effect of heparin on the increase of transfection efficiency was examined. Luciferase activity was significantly increased by the addition of 50 U/ml.

Example 4

Heparan Sulfate

Instead of heparin as in Examples 1-3, heparan sulfate (available from SEIKAGAKU INDUSTRY INC., and Sigma-Aldrich Japan) is used to demonstrate similar effects with the use of HVJ, influenza virus vector and adeno-associated virus vector.

As a result, when using heparan sulfate, it is confirmed that the gene delivery efficiency into the brain is enhanced. Accordingly, it is demonstrated that glucosaminoglycan in general is effective in the present invention.

Example 5

Chondroitin Sulfate

Instead of heparin as in Examples 1-3, chondroitin sulfate (available from SEIKAGAKU INDUSTRY INC., and Sigma-Aldrich Japan) is used to demonstrate similar effects of the use of HVJ, influenza virus vector and adeno-associated virus vector.

As a result, when using chondroitin sulfate, it is confirmed that the gene delivery efficiency into the brain is enhanced. Accordingly, it is demonstrated that glycosaminoglycans in general including glucosaminoglycan and galactosaminoglycan are effective in the present invention.

Although certain preferred embodiments have been described herein, it is not intended that such embodiments be construed as limitations on the scope of the invention except as set forth in the appended claims. It should be understood that all patents, published patent applications and publications cited herein are incorporated by reference as if set forth fully herein.

INDUSTRIAL APPLICABILITY

A method was provided for efficient delivery of a biomolecule into the brain and central nervous system (CNS) using a viral envelope both In vitro and in vivo. Further, a system and method were provided for highly efficient delivery of a biomolecule using a viral envelope. Accordingly, the present invention provides a technology for efficiently administering a biomolecule into the nervous system, which provides industrial applicability in that such technology can be applied to the administration of a variety of drugs.

The present invention can be produced as a composition by not only a medical doctor but also, for example, pharmaceutical entities and the like. Therefore, it is believed that the present invention is fully industrially applicable or has full utility. The present invention is also industrially applicable since it is useful as a clinical trial for business purposes in addition to a therapeutic method for pure medical purposes. Further, working of the method for treatment of the present invention in an indirect or direct manner is believed to have possibilities for use in the businesses medical service-related, and thus the present invention is industrially applicable or useful.

What is claimed is:

1. A system for introducing a biomolecule into a brain cell, comprising:
   1) a biomolecule contained in a viral envelope of inactivated Hemagglutinating Virus of Japan (HVJ) or inactivated Influenza virus, wherein said biomolecule is foreign to said virus; and
   2) heparin;
   wherein the heparin and the biomolecule and the viral envelope are contained in the same composition.

2. A method for introducing a biomolecule into a brain cell, comprising the steps of:
   A) administering to a brain cell a composition comprising a biomolecule contained in a viral envelope of inactivated HVJ or inactivated Influenza virus, wherein said biomolecule is foreign to said virus; and
   B) administering heparin to the cell,
   wherein said heparin is administered simultaneously with the administration of said composition such that the transfection efficacy into the brain cells of the composition is enhanced over administration of the composition without heparin.

* * * * *